United States Patent [19]

Falk

[11] 4,042,522
[45] Aug. 16, 1977

[54] AQUEOUS WETTING AND FILM FORMING COMPOSITIONS

[75] Inventor: Robert A. Falk, New City, N.Y.

[73] Assignee: Ciba-Geigy Corporation, Ardsley, N.Y.

[21] Appl. No.: 561,393

[22] Filed: Mar. 24, 1975

[51] Int. Cl.$^2$ .................. A62D 1/00; B27K 3/00; B01F 17/30
[52] U.S. Cl. .................... 252/8.05; 252/8.1; 252/356
[58] Field of Search .............. 252/8.05, 3, 8.1, 356; 21/60.5 A

[56] References Cited

U.S. PATENT DOCUMENTS

| | | | |
|---|---|---|---|
| 3,258,423 | 6/1966 | Tuve | 252/3 |
| 3,475,333 | 10/1969 | Meldrum | 252/3 |
| 3,562,156 | 2/1971 | Francen | 252/356 |
| 3,621,917 | 11/1971 | Rosen | 252/356 |
| 3,655,555 | 4/1972 | Rossmy | 252/8.05 |
| 3,766,274 | 10/1973 | Anello | 252/8.1 |
| 3,772,195 | 11/1973 | Francen | 252/356 |
| 3,839,425 | 10/1974 | Bartlett | 252/3 |
| 3,849,315 | 11/1974 | Chiesa | 252/3 |

*Primary Examiner*—Samuel W. Engle
*Assistant Examiner*—Donald P. Walsh
*Attorney, Agent, or Firm*—Nestor W. Shust

[57] ABSTRACT

The disclosure relates to aqueous compositions which comprise amphoteric fluorinated surfactant, anionic fluorinated surfactant, ionic non-fluorochemical surfactant, non-ionic, non-fluorochemical surfactant and optionally solvent. This composition is a concentrate which, when diluted with water, spreads on fuel surfaces suppressing vaporization. Because of this property the aqueous solutions of the above compositions are effective as fire fighting agents.

6 Claims, No Drawings

AQUEOUS WETTING AND FILM FORMING COMPOSITIONS

BACKGROUND OF THE INVENTION

It is well-known that so-called fluorochemical surfactants or $R_f$-surfactants reduce the surface tension of aqueous and non-aqueous solutions to a much greater degree than conventional hydrocarbon surfactants. While surface tensions of aqueous solutions containing non-hydrocarbon surfactants never go below 22 – 24 dynes/cm, it is possible with $R_f$-surfactants to achieve surface tensions as low as 15 dynes/cm. It is also well-known that synergistic surface tension effects are achieved from mixtures of different types of $R_f$-surfactants, as for instance nonionic and anionic $R_f$-surfactants, alone or in combination with classical hydrocarbon co-surfactants as told by Bernett and Zisman (Reference 1). Tuve et al in U.S. Pat. No. 3,258,423 also disclose the use of aqueous solutions of certain $R_f$-surfactants or $R_f$-surfactant mixtures alone or in combination with solvents and other additives as efficient fire fighting agents. Based on the Tuve et al findings many other fire fighting agents containing different $R_f$-surfactant systems have been disclosed as shown in U.S. Pat. No. 3,315,326 and 3,772,195.

Fire fighting agents containing $R_f$-surfactants act in two ways:

a. As foams, they are used as primary fire extinguishing agents.

b. As vapor sealants, they prevent the re-ignition of fuels and solvents.

It is this second property which makes fluorochemical fire fighting agents far superior to any other known fire fighting agent.

These $R_f$-surfactant fire fighting agents are commonly known as AFFF (standing for Aqueous Film Forming Foams). AFFF agents act the way they do because the $R_f$-surfactants reduce the surface tension of aqueous solutions to such a degree that the solutions will wet and spread upon non-polar and water immiscible solvents even though such solvents are lighter than water; they form a fuel or solvent vapor barrier which will rapidly extinguish flames and prevent re-ignition and reflash. The criterion necessary to attain spontaneous spreading of two immiscible phases has been taught by Harkins et al, J. Am. Chem. 44, 2665 (1922). The measure of the tendency for spontaneous spreading is defined by the spreading coefficient (SC) as follows:

$SC = \gamma a - \gamma b - \gamma i$ where

SC = spreading coefficient
$\gamma a$ = surface tension of the lower liquid phase
$\gamma b$ = surface tension of the upper aqueous phase
$\gamma l$ = interfacial tension between the aqueous upper phase and lower liquid phase.

If the SC is positive, the surfactant solution should spread and film formation should occur. The greater the SC, the greater the spreading tendency. This requires the lowest possible aqueous surface tension and lowest interfacial tension, as is achieved with mixtures of certain $R_f$-surfactant(s) and classical hydrocarbon surfactant mixtures.

Commercial AFFF agents are primarily used today in so-called 6% and 3% proportioning systems. 6% means that 6 parts of an AFFF agent and 94 parts of water (fresh sea, or brackish water) are mixed or proportioned and applied by conventional foam making equipment wherever needed. Similarly an AFFF agent for 3% proportioning is mixed in such a way that 3 parts of this agent and 97 parts of water are mixed and applied.

Today AFFF agents are used wherever the danger of fuel solvent fires exist and especially where expensive equipment has to be protected. They can be applied in many ways, generally using conventional portable handline foam nozzles, but also by other techniques such as with oscillating turret foam nozzles, subsurface injection equipment (petroleum tank farms), fixed non-aspirating sprinkler systems (chemical process areas, refineries), underwing and overhead hangar deluge systems, inline proportioning systems (induction metering devices), or aerosol type dispensing units as might be used in a home or vehicle. AFFF agents are recommended fire suppressants for Class A or Class B flammable solvent fires, particularly the latter. Properly used alone or in conjunction with dry chemical extinguishing agents (twin-systems) they generate a vapor-blanketing foam with remarkable securing action.

AFFF agents generally have set a new standard in the fighting of fuel fires and surpass by far any performance of the previously used protein foams. However, the performance of today's commercial AFFF agents is not the ultimate as desired by the industry. The very high cost of AFFF agents is limiting a wider use and it is, therefore, mandatory that more efficient AFFF agents which require less fluorochemicals to achieve the same effect are developed. Furthermore, it is essential that secondary properties of presently available AFFF agents be improved. The new AFFF agents should have: (a) a lower degree of toxicity (fish toxicity is a very essential element whenever AFFF agents are dispensed in large quantities and when there is a chance that such agents might pollute receiving streams and lakes; this is a major problem on test grounds where AFFF agents are often used); (b) a lower chemical oxygen demand (COD); good biodegradability (so as not to hinder the activity of microorganisms in biological treatment systems); (c) a less corrosive character so that they can be used in light weight containers made of aluminum rather than heavy, non-corrosive alloys: (d) improved long term storage stability; (e) good compatibility properties with conventional dry chemical extinguishers; (f) an improved vapor sealing characteristic and seal speed, and most importantly; (g) have such a high efficiency that instead of using 3 and 6% proportioning systems it might become possible to use AFFF agents in 1% or lower proportioning systems. This means that 1 part of an AFFF agent can be blended or diluted with 99 parts of water. Such highly efficient concentrates are of importance because storage requirements of AFFF agents will be greatly reduced, or in the case where storage facilities exist, the capacity of available fire protection agent will be greatly increased. AFFF agents for 1% proportioning systems are of great importance therefore wherever storage capacity is limited such as on offshore oil drilling rigs, offshore atomic power stations, city fire trucks and so on. The performance expected from an AFFF agent today is in most countries regulated by the major users such as the military and the most important AFFF specifications are documented in the U.S. Navy Military Specification MIL-F-24385 and its subsequent amendments.

The novel AFFF agents described of this invention are in comparison with today's AFFF agents superior not only with regard to the primary performance characteristics such as control time, extinguishing time and burnback resistance but additionally, because of their very high efficiency offer the possibility of being used in 1% proportioning systems. Furthermore, they offer desirable secondary properties from the standpoint of ecology as well as economy.

DETAILED DISCLOSURE

The present invention is directed to aqueous film forming concentrate compositions for extinguishing or preventing fires by suppressing the vaporization of flammable liquids, said composition comprising
A. 0.5 to 25% by weight of amphoteric fluorinated surfactant,
B. 0.1 to 5% by weight of anionic fluorinated surfactant,
C. 0.1 to 25% by weight of ionic non-fluorochemical surfactant
D. 0.1 to 40% by weight of nonionic non-fluorochemical surfactant,
E. 0 to 70% by weight of solvents, and
F. water in the amount to make up the balance of 100%.

To form effective compositions, a mixture of various surfactants must attain surface tensions of less than about 26 dynes/cm. Each component (A) to (E) may consist of a specific compound or a mixture of compounds.

The above composition is a concentrate which, as noted above, when diluted with water, forms a very effective fire fighting formulation by forming a foam which deposits a tough film over the surface of the flammable liquid which prevents its further vaporization and this extinguishes the fire.

It is a preferred fire extinguishing agent for flammab solvent fires, particularly for hydrocarbons and polar solvents of low water solubility, in particular for:
Hydrocarbon Fuels - such as gasoline, heptane, toluene, hexane, Avgas, VMP naphtha, cyclohexane, turpentine, and benzene;
Polar Solvents of Low Water Solubility - such as butyl acetate, methyl isobutyl ketone, butanol, ethyl acetate, and
Polar Solvents of High Water Solubility - such as methanol, acetone, isopropanol, methyl ethyl ketone, ethyl cellosolve and the like.

It may be used concomitantly or successively with flame suppressing dry chemical powders such as sodium or potassium bicarbonate, ammonium dihydrogen phosphate, $CO_2$ gas under pressure, or Purple K, as in so-called Twin-agent systems. A dry chemical to AFFF agent ratio would be from 10 to 30 lbs of dry chemical to 2 to 10 gallons AFFF agent in use concentration (i.e. after 0.5%, 1%, 3%, 6% or 12% proportioning). In a typical example 20 lbs of a dry chemical and 5 gals. of AFFF agent could be used. The composition of this invention could also be used in conjunction with hydrolyzed protein or fluoroprotein foams.

The foams of the instant invention do not disintegrate or otherwise adversely react with a dry powder such as Purple-K Powder (P-K-P). Purple-K Powder is a term used to designate a potassium bicarbonate fire extinguishing agent which is free-flowing and easily sprayed as a powder cloud on flammable liquid and other fires.

The concentrate is normally diluted with water by using a proportioning system such as, for example, a 3% or 6% proportioning system whereby 3 parts or 6 parts of the concentrate is admixed with 97 or 94 parts respectively of water. This highly diluted aqueous composition is then used to extinguish and secure the fire.

The amphoteric fluorinated surfactants employed in the compositions of this invention as component (A) can be represented by the formulae:

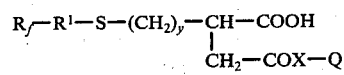

and its isomer

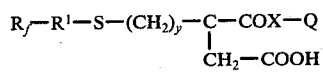

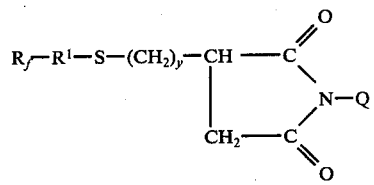

wherein
$R_f$ is straight or branched chain perfluoroalkyl of 1 to 18 carbon atoms or said perfluoroalkyl substituted by perfluoroalkoxy of 2 to 6 carbon atoms,
$R^1$ is branched or straight chain alkylene of 1 to 12 carbon atoms, alkylenethioalkylene of 2 to 12 carbon atoms, alkyleneoxyalkylene of 2 to 12 carbon atoms or alkyleneiminoalkylene of 2 to 12 carbon atoms where the nitrogen atom contains as a third substituent, hydrogen or alkyl of 1 to 6 carbon atoms,
$y$ is 1 or zero,
X is oxygen or -NR, wherein R is hydrogen, lower alkyl of 1 to 6 carbon atoms, hydroxy-alkyl of 1 to 6 carbon atoms, or R together with Q forms a piperazine ring, and
Q is a nitrogen containing group selected from
1. an aliphatic amino group selected from

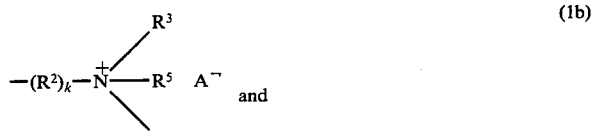

wherein
$R^2$ is a linear or branched alkylene of 2 to 12 carbon atoms, oxygen or sulfur interrupted linear or branched alkylene of up to 60 carbon atoms, or hydroxyl substituted alkylene. Preferably $R^2$ is a straight chain or branched alkylene of 2 to 5 carbon atoms;
$k$ is 1 or zero, with the provision, that if X is oxygen, $k$ is 1;
$R^3$ and $R^4$ are independently of each other hydrogen, alkyl group, substituted alkyl group of 1 to 20 carbon atoms; phenyl group, alkyl or halogen substituted phenyl group of 6 to 20 carbon atoms, polyethoxy or polypropoxy group of 2 to 20 alkoxy units with the proviso that if X is oxygen, $R^3$ and $R^4$ are not hydrogen. The alkyl substituents can be alkyl of 1 to 5 carbon atoms, dienyl, hydroxyl, carboxyl, halogen, alkylene dialkylphosphonate such as methylene-diethylphosphonate or a group

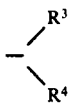

Phenyl substituents can be methyl, halogen or hydroxyl. Preferably $R^3$ and $R^4$ are alkyl groups of 1 to 4 carbons.

$A^-$ is any anion which forms an ammonium salt of the formula $NH_4^+A^-$ having a solubility in water of at least about 1%.

Anion $A^-$ is derived from alkyl halides, benzene or chlorobenzene sulfonate esters of alkyl alcohols and methyl and ethyl sulfates. $A^-$ is preferably $Cl^-$ or $CH_3CH_2OSO_3^-$.

$R^5$ is hydrogen, an alkyl group or hydroxylalkyl group, aralkyl or groups of the formula $-(CH_2)_n-COO$-alkyl, said alkyl group having 1 to 18 carbons. Preferably, $R^5$ is methyl, ethyl, propyl, butyl or benzyl.

$G^-$ is selected from the groups

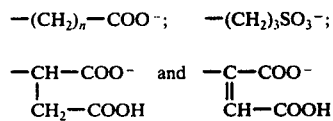

where n is 1 to 5;

2. cyclic amino groups selected from

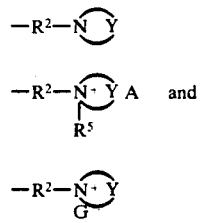

wherein Y is a diradical group of the formulae:
—$(CH_2)_4$—
—$(CH_2)_5$—
—$(CH_2)_2$-O-$(CH_2)_2$—

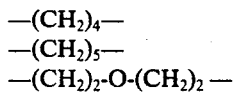
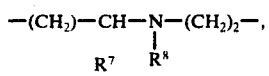

wherein $R^2$, $R^5$, $A^-$ and $G^-$ are as defined above, $R^7$ and $R^8$ are independent hydrogen, a lower alkyl or hydroxy-lower alkyl group of 1 to 6 carbon atoms, with the provision, that if X is oxygen, $R^8$ cannot be hydrogen.

3. aromatic amino groups selected from

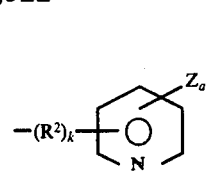

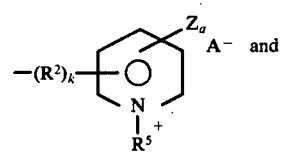

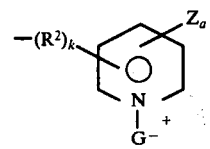

4. fused-ring aromatic amino group selected from

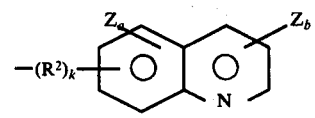

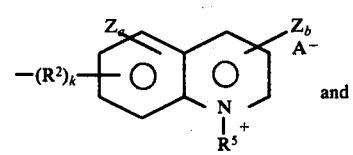

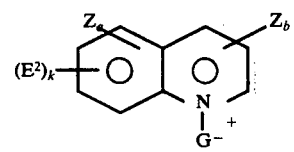

wherein
Z is halogen or methyl,
$a + b$ is an integer from 0–3; and
5. a heterocyclic amino group of the formula
5a. —$(R^2)_k$-E
5b. —$(R^2)_k$-E$^+$-$R^5$ $A^-$
5c. —$(R^2)_k$-E$^+$-$G^-$ where k is one or zero and E is selected from N-hydroxyalkyl or N-amino-alkyl, substituted pyrrole, pyrazole, imidazole, triazole, indole or indazole, hydroxyalkyl and aminoalkyl ring-substituted pyridazine, pyrimidino, pyrazino or quinoxalino.

Illustrative examples of amphoteric fluorinated surfactants are:

N-[3-(dimethylamino)propyl]-2,(3)-(1,1,2,2-tetrahydroperfluoroalkylthio)succinamic acid, N-methyl-N-(2'-N',N'-dimethylaminoethyl)-2,(3)-(1,1,2,2-tetrahydroperfluoroalkylthio)succinamic acid, N-(2-dimethylaminoethyl)-2,(3)-(1,1,2,2'-tetrahydroperfluoroalkylthio)succinamic acid, 2-(3)-(1,1,2,2-tetrahydroperfluorodecylthio)succinic acid-mono-[2-(N,N-methyl)aminoethyl]ester, 2-(3)-(1,1,2,2-tetrahydroperfluorodecylthio)succinic acid-mono-(2'-quinolino ethyl)ester, N,N'-bis[(n-propyl-3)-(1,1,2,2-tetrahydroperfluorooctylthio)succinamic monoamido]piperazine, N-[3-(dimethylamino)propyl]-2,(3)-(heptafluoroisopropoxy-1,1,2,2-tetrahydroperfluoroalkylthio)succinamic acid, 2-(1,1,2,2,-tetrahydroperfluoroctylthio)N-[3-dimethylamine)propyl]-2-methyl succinamic acid.

N-ethyl-N-(2'-N',N'-dimethylaminoethyl)-2,(3)-(1,1,2,2-tetrahydroperfluoroalkylthio)succinamic acid, N-methyl-N-(2'-N',N'-dimethylaminopropyl)-2,(3)-(1,1,2,2-tetrahydroperfluoroalkylthio)succinamic acid, N-[3-(dimethylamino)propyl]-2(3)-(1,1,2,2-tetrahydroperfluorooctylthio)succinamic acid, N-[3-(dimethylamino)propyl]-2(3)-(1,1,2,2-tetrahydroperfluorodecylthio)succinamic acid, and N-[3-(dimethylamino)propyl]-2(3)-(1,1,2,2-tetrahydroperfluorododecylthio)succinamic acid, Reaction product of N-[3-(dimethylamino)propyl]-](3)-(1,1,2,2-tetrahydroperfluorodecylthio)succinamic acid and propane sultone Reaction product of N-[3-(dimethylamino)propyl]-2(3)-(1,1,2,2-tetrahydroperfluorooctylthio)succinamic acid and chloroacetic acid.

The above amphoterics are disclosed more fully in the copending application of Karl F. Mueller, filed Jan. 3, 1975, Ser. No. 538,432 which is incorporated herein by reference.

Component (B) is a fluorinated anionic surfactant. The exact structure of these surfactants is not critical and they may be chosen from compositions wherein the fluoroaliphatic surfactant is a water soluble fluoroaliphatic compound represented by the formula $$R_f Q_m Z$$

wherein $R_f$ is a fluorinated saturated monovalent non-aromatic radical containing from 3 to 20 carbon atoms in which the carbon atoms of the chain are substituted only by fluorine, chlorine or hydrogen atoms with no more than one hydrogen or chlorine atom for every two carbon atoms, and in which a divalent oxygen or trivalent nitrogen atom, bonded only to carbon atoms, can be present in the skeletal chain;

$Q_m$, where m is an integer of 0 or 1, is a multivalent linking group comprising alkylene, sulfonamido alkylene and carbonamido alkylene radicals; and Z is a water solubilizing polar group comprising anionic radicals.

Preferred anionic groups are $-CO_2^-$ and $-SO_3^-$. The anionic surfactant should contain 30–65% of carbon bound fluorine in order to attain suitable solubility properties. The anionic surfactant may be present as free acid, an alkali metal salt thereof, ammonium, or substituted ammonium.

Illustrative examples of $R_f$-anionics which can be used in the compositions of this invention are the below shown acids and their alkali metal salts. The patent numbers appearing in parenthesis are patents which more fully disclose the represented class of compounds. The disclosures of these patents are incorporated herein by reference.

| Carboxylic Acids and Salts thereof | |
|---|---|
| $R_f COOH$ | (Scholberg et al, J. Phys. Chem. 57, 923–5(1953)) |
| $R_f(CH_2)_{1-20}COOH$ | (Ger. 1,916,669) |
| $R_f O(CF_2)_{2-20}COOH$ | (Ger. 2,132,164) |
| $R_f O(CF_2)_{2-20}(CH_2)_{2-20}COOH$ | (Ger. 2,132,164) |
| $R_f O(CH_2)_{1-20}COOH$ | (U.S. 3,409,647) |
| $R_f SO_2N(C_2H_5)CH_2COOH$ | (U.S. 3,258,423) |
| $R_f O(CF_2O)_3CF_2COOH$ | (Fr. 1,531,902) |

| -continued | |
|---|---|
| $R_f O \left( \begin{array}{c} CF_2CFO \\ \mid \\ CF_3 \end{array} \right) CF_2COOH$ | (Fr. 1,537,922) |
| $R_f O[CF(CF_3)CF_2O]CF(CF_3)CON(CH_3)CH_2COOH$ | (U.S. 3,798,265) |
| $(C_2F_5)_2(CF_3)CCH_2COOH$ | (Brit. 1,176,493) |
| $C_{10}F_{19}OC_6H_4CON(CH_3)CH_2COOH$ | (Brit. 1,270,662) |
| $R_f(CH_2)_{1-3}SCH(COOH)CH_2COOH$ | (U.S. 3,706,787) |
| $R_f(CH_2)_{1-12}S(CH_2)_{1-17}COOH$ | Ger. 2,239,709; U.S. 3,172,910 |

| Sulfonic Acids and Salts Thereof | |
|---|---|
| $R_f SO_3H$ | (U.S. 3,475,333) |
| $R_f C_6H_4SO_3H$ | (Ger. 2,134,973) |
| $R_f(CH_2)_{1-20}SO_3H$ | (Ger. 2,309,365) |
| $R_f SO_2NHCH_2C_6H_4SO_3H$ | (Ger. 2,315,326) |
| $R_f SO_2N(CH_3)(C_2H_4O)_{1-20}SO_3H$ | (S.A. 693,583) |
| $R_f CH_2CH_2OCH_2CH_2CH_2SO_3H$ | (Can. 842,252) |
| $R_f OC_6H_4SO_3H$ | (Ger. 2,230,366) |
| $C_{12}F_{23}OC_6H_4SO_3H$ | (Ger. 2,240,263) |
| $(C_2F_5)_3CO(CH_2)_3SO_3H$ | (Brit. 1,153,854) |
| $CF_3(C_2F_5)_2CO(CH_2)_3SO_3H$ | (Brit. 1,153,854) |
| $(C_2F_5)_2(CF_3)CCH=C(CF_3)SO_3H$ | (Brit. 1,206,596) |
| $R_f OCF(CF_3)CF_2OCF(CF_3)CONHCH_2SO_3H$ | (U.S. 3,798,265) |

| Phosphonates, Phosphates, Related Phosphoro Derivatives, and Salts Thereof | |
|---|---|
| $R_f PO(OH)_2$, $(R_f)_2PO(OH)$ | (Ger. 2,110,767) |
| $R_f SO_2N(Et)C_2H_4OPO(OH)_2$ | (Ger. 2,125,836) |
| $R_f CH_2OPO(OH)_2$ | (Ger. 2,158,661) |
| $C_8F_{15}OC_6H_4CH_2PO(OH)_2$ | (Ger. 2,215,387) |
| $R_f OC_6H_4CH_2PO(OH)_2$ | (Ger. 2,230,366) |

| Others (and Salts Thereof) | |
|---|---|
| $R_f SO_2N(CH_3)C_2H_4OSO_3H$ | (Ger. 1,621,107) |
| $R_f C_6H_4OH$ | (U.S. 3,475,333) |
| $R_f(CH_2)_{1-20}S_2O_3Na$ | (Ger. 2,115,139) |
| $R_f(CH_2)_{1-20}SO_2N(CH_3)CH_2CH_2S_2O_3Na$ | (Ger. 2,115,139) |
| $R_f \ldots SO_2H$ | (U.S. 3,562,156) |

In the sulfonate class of the fluorinated anionic surfactants a particularly preferred type of compounds are sulfonates formed by the reaction of 1,3-propane sultone and a perfluoroalkylthiol and have the structure $$R_f-R^1-S-(CH_2)_3SO_3^-Z^+$$

wherein $R_f$ and Z are as defined above and R is as defined below

The perfluoroalkyl thiols employed in the preparation of the sultones are well known in the prior art. For example, thiols of the formula $R_f R^1$-SH have been described in a number of U.S. Pat. Nos. including 2,894,991; 2,961,470; 2,965,677; 3,088,849; 3,172,190; 3,544,663; and 3,655,732.

Thus, U.S. Pat. No. 3,655,732 discloses mercaptans of formula $$R_f-R^1-SH$$

where $R^1$ is alkylene of 1 to 16 carbon atoms and $R_f$ is perfluoroalkyl and teaches that halides of formula $R_f$-$R^1$-hal are well known; reaction of $R_f I$ with ethylene under freeradical conditions gives $R_f(CH_2CH_2)_a I$ while reaction of $R_f CH_2 I$ with ethylene gives $R_f CH_2(CH_2CH_2)_a I$ as is further taught in U.S. Pat. Nos. 3,088,849; 3,145,222; 2,965,659 and 2,972,638.

U.S. Pat. No. 3,655,732 further discloses compounds of formula $$R_f-R^1-X-R''-SH$$

where $R^1$ and $R''$ are alkylene of 1 to 16 carbon atoms, with the sum of the carbon atoms of $R^1$ and $R''$ being no greater than 25; $R_f$ is perfluoroalkyl of 4 through 14

U.S. Pat. No. 3,485,806 and Brit. Pat. No. 1,181,218 which are also incorporated herein by reference.

Of the above-mentioned aminimides, the carboxaminimides are most preferred because of the combination of very desirable surface active properties listed below:

a. they are highly surface active and possess very low interfacial tensions at low concentrations and hence afford films of exceedingly highspreading coefficient;
b. they are amphoteric and thus compatible with all types of fluorosurfactants -anionic, cationic, non-ionic, or amphoteric;
c. they are thermally stable at practically useful application and storage temperatures;
d. they are acid and alkali stable;
e. they are biodegradable and non-toxic;
f. they are readily dispersible in water;
g. they are high-foaming and only moderately affected by water hardness;
h. they are inexpensive and commercially available.

Illustrative examples of the non-fluorochemical amphoteric surfactants are:

| | |
|---|---|
| coco fatty betaine ($CO_2^-$) | (Velvetex BC) |
| cocoylamidoethyl hydroxyethyl carboxymethyl glycine betaine | (Velvetex CG) |
| cocylamidoammonium sulfonic acid betaine | (Sulfobetaine CAW) |
| cetyl betain (C-type) | (Product BCO) |
| a sulfonic acid betaine derivative | (Sulfobetaine DLH) |
| $C_{11}H_{23}CONN(CH_3^{-+})_2CHOHCH_3$ | (Aminimides) A56203 |
| $C_{13}H_{27}CONN(CH_3^{-+})_2CH_2CHOHCH_3$ | (A56403) |
| $C_{15}H_{31}CONN^{-+}(CH_3)_2CH_2CHOHCH_3$ | (A56603) |
| $C_{17}H_{35}CONN^{-+}(CH_3)_2CH_2CHOHCH_3$ | (A56803) |
| $C_{11}H_{23}CONN^{-+}(CH_3)_3$ | (A56201) |
| $C_{13}H_{27}CONN^{-+}(CH_3)_3$ | (A56401) |
| $C_{15}H_{31}CONN^{-+}(CH_3)_3$ | (A56601) |
| $C_{11}H_{23}C\underset{+N}{\overset{N}{\parallel}}\begin{array}{c}CH_2\\ \diagdown\\ CH_2 \\ \diagup \\ \end{array}\begin{array}{c}CH_2\\ \diagup\\ \diagdown \\ CH_2CO_2Na\end{array}CH_2CH_2OCH_2CO_2^-$ | (Miranol H2M-SF) |
| A coco-derivative of the above | (Miranol CM-SF) |
| Coco Betaine | (Lonzaine 12C) |
| $C_{12-14}H_{25-29}{}^+NH_2CH_2CH_2COO^-$ (triethanolammonium salt) | (Deriphat 170C) |
| $C_{12}H_{25}\underset{H}{\overset{+}{N}}\diagup^{CH_2CH_2CO_2^-}\diagdown_{CH_2CH_2CO_2Na}$ | (Deriphat 160C) |

A nonionic non-fluorochemical surfactant component (D) is incorporated in the aqueous fire composition primarily as a stabilizer and solubilizer for the compositions, particularly when they are diluted with hard water or sea water. The nonionics are chosen primarily on the basis of their hydrolytic and chemical stability, solubilization and emulsification characteristics (e.g. measured by HLB-hydrophic-lipophilic balance), cloud point in high salt concentrations, toxicity, and biodegradation behavior. Secondarily, they are chosen with regard to foam expansion, foam viscosity, foam drainage, surface tension, interfacial tension and wetting characteristics.

Typical classes of nonionic sufactants useful in this invention include polyoxyethylene derivatives of alkylphenols, linear or branched alcohols, fatty acids, mercaptans, alkylamines, alkylamides, acetylenic glycols, phosphorus compounds, glucosides, fats and oils. Other nonionics are amine oxides, phosphine oxides and nonionics derived from block polymers containing polyoxyethylene and/or polyoxypropylene units.

Preferred are polyoxyethylene derivatives of alkylphenols, linear or branched alcohols, glucosides and block polymers of polyoxyethylene and polyoxypropylene, the first two mentioned being most preferred.

Illustrative examples of the non-ionic non-fluorochemical surfactants are

| | |
|---|---|
| Octylphenol$(EO)_{9,10}$ | (Triton X-100) |
| " $(EO)_{16}$ | (Triton X-165) |
| " $(EO)_{30}$ | (Triton X-305) |
| Nonylphenol $(EO)_{9,10}$ | (Triton N-101) |
| " $(EO)_{12,13}$ | (Triton N-128) |
| Lauryl ether $(EO)_{23}$ | (Brij 35) |
| Stearyl ether $(EO)_{10}$ | (Brij 76) |
| Sorbitan monolaurate $(EO)_{20}$ | (Tween 20) |
| Dodecylmercaptan $(EO)_{10}$ | (Tergitat 12-M-10) |
| Block copolymer of $(EO)_x(PO)_4$ | (Pluronic F-68) |
| Block copolymer | (Tetronic 904) |
| $C_{11}H_{23}CON(C_2H_4OH)_2$ | (Superamide L9) |
| $C_{12}H_{25}N(CH_3)_2O$ | (Ammonyx LO) |
| $C_{12}H_{25}N\diagup^{(CH_2CH_2O)_xH}\diagdown_{(CH_2CH_2O)_yH}$ $x+y=25$ | (Ethomeen C/$_{25}$) |

NOTE: EO used above means ethylene oxide repeating unit.

Component (E) is a solvent which acts as an antifreeze, a foam stabilizer or as a refractive index modifer so that proportioning systems can be field calibrated. Actually, this is not a necessary component in the composition of this invention since very effective AFFF concentrates can be obtained in the absence of a solvent. In fact, this is one of the unexpected and unusual features of this invention since prior art compositions as a rule must employ a relatively high percentage of a solvent. However, even with the compositions of this invention it is often advantageous to employ a solvent especially if the AFFF concentrate will be stored in subfreezing temperatures. Useful solvents are disclosed in U.S. Pat. NOS. 3,457,172; 3,422,011; and 3,579,446, and German patent 2,137,711.

Typical solvents are alcohols or ethers such as:
ethylene glycol monoalkyl ethers,
diethylene glycol monoalkyl ethers,
propylene glycol monoalkyl ethers,
dipropylene glycol monoalkyl ethers,
triethylene glycol monoalkyl ethers,
1-butoxyethoxy-2-propanol, glycerine, diethyl carbitol, hexylene glycol, butanol,
t-butanol, isobutanol, ethylene glycol
and other low molecular weight alcohols
such as ethanol or isopropanol wherein
the alkyl groups contain 1-6 carbon atoms.

Preferred solvents are 1-butoxyethoxy-2-propanol, diethyleneglycol monobutyl ether, or hexylene glycol.

Still other components which may be present in the formulation are:

--Buffers whose nature is essentially non-restricted and which are exemplified by Sorensen's phosphate or McIlvaine's citrate buffers.

--Corrosion inhibitors whose nature is non-restricted so long as they are compatible with the other formulation ingredients.

--Chelating agents whose nature is non-restricted, and which are exemplified by polyaminopolycarboxylic acids, ethylenediaminetetraacetic acid, citric acid, gluconic acid, tartaric acid, nitrilotriacetic acid, hydroxyethylethylenediaminetriacetic acid and salts thereof.

carbon atoms and X is -S- or -NR'''-where R''' is hydrogen or alkyl of 1 through 4 carbon atoms.

The reaction of the iodide $R_f R^1$-I with thiourea followed by hydrolysis to obtain the mercaptan $R_f R^1$-SH is the preferred synthetic route. The reaction is applicable to both linear and branched chain iodides. Many useful perfluoroalkoxyalkyl iodides are described in Australian Application 36868, filed Apr. 24, 1968, of general formula:

$$(CF_3)_2CFO\ CF_2CF_2(CH_2CH_2)_mI$$

where m is 1-3.

Particularly preferred herein are the thiols of formula:

$$R_f CH_2CH_2SH$$

where $R_f$ is perfluoroalkyl of 6 to 12 carbon atoms. These $R_f$-thiols can be prepared from $R_f CH_2CH_2I$ and thiourea in very high yield.

Component (c), an ionic non-fluorochemical water soluble sufactant is chosen from the anionic, cationic or amphoteric surfactants as represented in the tabulations contained in Rosen et al, *Systematic Analysis of Surface-Active Agents*, Wiley-Interscience, New York, (2nd edition, 1972), pp. 485-544, which is incorporated herein by reference.

It is particularly convenient to use amphoteric or anionic fluorine-free surfactants because they are relatively insensitive to the effects of fluoroaliphatic surfactant structure or to the ionic concentration of the aqueous solution and furthermore, are available in a wide range of relative solubilities, making easy the selection of appropriate materials.

Preferred ionic non-fluorochemical surfactants are chosen with primary regard to their exhibiting an interfacial tension below 5 dynes/cm at concentrations of .01-.3% by weight. They should also exhibit high foam expansions at their use concentration, be thermally stable at practically useful application and storage temperatures, be acid and alkali resistant, be readily biodegradable and non-toxic, especially to aquatic life, be readily dispersible in water, be unaffected by hard water or sea water, be compatible with anionic or cationic systems, form protective coatings on materials of construction, be tolerant of pH, and be available commercially and inexpensive.

In accordance with the classification scheme contained in Schwartz et al, *Surface Active Agents*, Wiley-Interscience, N.Y., 1963, which is incorporated herein by reference, anionic and cationic surfactants are described primarily according to the nature of the solubilizing or hydrophilic group and secondarily according to the way in which the hydrophilic and hydrophobic groups are joined, i.e. directly or indirectly, and if indirectly according to the nature of the linkage.

Amphoteric surfactants are described as a distinct chemical category containing both anionic and cationic groups and exhibiting special behavior dependent on their isoelectric pH range, and their degree of charge spearation.

Typical anionic surfactants include carboxylic acids, sulfuric esters, alkane sulfonic acids, alkylaromatic sulfonic acids, and compounds with other anionic hydrophilic functions, e.g., phosphates and phosphonic acids, thiosulfates, sulfinic acids, etc.

Preferred are carboxylic or sulfonic acids since they are hydrolytically stable and generally available. Illustrative examples of the anionic surfactants are

| | |
|---|---|
| $C_{11}H_{23}O(C_2H_4O)_{3.5}SO_3Na$ | (Sipon ES) |
| $C_{11}H_{23}OCH_2CH_2OSO_3Na$ | (Sipon ESY) |
| $C_{12}H_{25}OSO_3Na$ | (Duponol QC) |
| Disodium salt of alkyldiphenyl ether disulfonate | Dowfax 3B2 |
| Disodium salt of sulfosuccinic acid half ester derived from a $C_{10-12}$ ethoxylated alcohol | (Aerosol A-102) |
| Sodium Alpha olefin sulfonates | (Bioterge AS-40) |
| $C_{11}H_{23}CONH(CH_3)C_2H_4SO_3Na$ | (Igepon TC42) |
| $C_{11}H_{23}CON(CH_3)CH_2CO_2Na$ | (Sarkosyl NL-97) |

Typical cationic classes include amine salts, quaternary ammonium compounds, other nitrogenous bases, and non-nitrogenous bases, e.g. phosphonium sulfonium, sulfoxonium; also the special case of amine oxides which may be considered cationic under acidic conditions.

Preferred are amine salts, quaternary ammonium compounds, and other nitrogenous bases on the basis of stability and general availability. Non-halide containing cationics are preferred from the standpoint of corrosion. Illustrative examples of the cationic surfactants are

| | |
|---|---|
| bis(2-hydroxyethyl)tallowamine oxide | (Aromox T/12) |
| dimethyl hydrogenated tallowamine oxide | (Aromox DMHT) |
| isostearylimidazolinium ethosulfate | (Monaquat ISIES) |
| cocoylimidazolinium ethosulfate | (Monaquat CIES) |
| lauroylimidazolinium ethosulfate | (Monaquat LIES) |

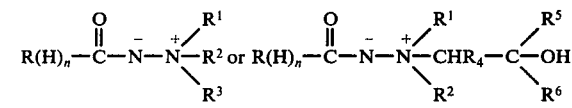

(Catanac 609)

[$C_{11}H_{23}CONH(CH_2)_3N(CH_3)_3]^+CH_3SO_4$  (Catanac LS)
[$C_{17}H_{35}CONH(CH_2)_3N(CH_3)_2CH_2CH_2OH]^+ \lambda NO_3-$  (Catanac SN)

The amphoteric non-flourochemical surfactants include compounds which contain in the same molecule the following groups: amino and carboxy, amino and sulfuric ester, aminor and alkane sulfonic acid, amino and aromatic sulfonic acid, miscellaneous combinations of basic and acidic groups, and the special case of aminimides.

Preferred non-fluorochemical amphoterics are those which contain amino and carboxy or sulfo groups, and the aminimides.

The aminimide surfactants have been described in *Chemical Reviews Vol. 73*, No. 3(1973) which is incorporated herein by reference. Generally, they are the carboxaminimides of the general formulae:

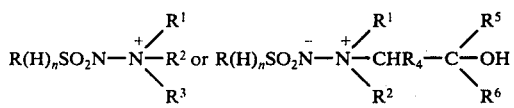

and sulfonylaminimides of the general formulae:

$$R(H)_nSO_2N \overset{+}{-} \overset{R^1}{\underset{R^3}{N{<}R^2}} \text{ or } R(H)_nSO_2N \overset{-}{-} \overset{+}{N} \overset{R^1}{\underset{R^2}{<}} CHR_4 \overset{R^5}{\underset{R^6}{-}C{-}OH}$$

aminocyanoimides, aminonitroimides, or functionally substituted aminimides as described in U.S. 3,499,032, —High molecular weight foam stabilizers such as polyethyleneglycol, hydroxypropyl cellulose, or polyvinylpyrrolidone.

The concentrates of this invention are effective fire fighting compositions at any pH level, but generally such concentrates are adjusted to a pH of 6 to 9, and more preferably to a pH of 7 to 8.5, with a dilute acid or alkali. For such purpose may be employed organic or mineral acids such as acetic acid, oxalic acid, sulfuric acid, phosphoric acid and the like or metal hydroxides or amines such as sodium or potassium hydroxides, triethanolamine, tetramethylammonium hydroxide and the like.

As mentioned above, the compositions of this invention are concentrates which must be diluted with water before they are employed as fire fighting agents. Although at the present time the most practical, and therefore preferred concentrations of said proportioning composition in water are 3% and 6% because of the availability of fire fighting equipment which can automatically admix the concentrate with water in such proportions, there is no reason why the concentrate could not be employed in a 0.5% to 3% proportioning system or in 6% to 12% proportioning system. It is simply a matter of convenience, the nature of fire and the desired effectiveness in extinguishing the flames.

An aqueous AFFF concentrate composition which would be very useful in a 6% proportioning system comprises A. 1.0 to 3.5% by weight of amphoteric fluorinated surfactant,
B. 0.1 to 2.5% by weight of anionic fluorinated surfactant,
C. 0.1 to 4.0% by weight of ionic non-fluorochemical surfactant,
D. 0.1 to 8.0% by weight of a nonionic non-fluorochemical surfactant,
E. 0 to 20% by weight of solvent and water in the amount to make up the balance of 100%.

The subject composition can be also readily dispersed from an aerosol-type container by employing a conventional inert propellant such as Freon 11, 12, 22 or C-318, $N_2O$, $N_2$ or air. Expansion volumes as high as 50 based on the ratio of air to liquid are attainable.

The most important elements in this new AFFF system are the amphoteric $R_f$-surfactants of component (A) which are disclosed in U.S. application Ser. No. 538,432 and which are defined below. These amphoteric $R_f$-sulfactants reduce surface tensions of the aqueous solutions to about 20 dynes/cm and act as solubilizers for the Type B $R_f$-sulfactants contributing to most of the excellent characteristics of the novel AFFF agents of this invention. The anionic $R_f$-surfactants of component (B) act as surface tension depressants for the amphoteric surfactant of component (A) (synergistic $R_f$-surfactant mixtures) depressing the surface tension to 15–16 dynes/cm and are usually present in a much lower concentration than the $R_f$-surfactants of component (A). $R_f$-surfactants of component (B) furthermore increase the spreading speed of aqueous AFFF films on hydrocarbon fuels and contribute significantly to the excellent resealing capacity of the novel AFFF agent. The ionic or amphoteric hydrocarbon sufactants of component (C) have a dual function. They act as interfacial tension depressants by reducing the interfactial tensions of the aqueous $R_f$-surfactant solution containing components (A) and (B) $R_f$-surfactants, from interfacial tensions as high as 10 dynes/cm to interfacial tensions as low as .1 dyne/cm. Furthermore, the cosurfactants of component (C) act as foaming agents and by varying the amount and proportions of component (C) cosurfactants, it is possible to vary the foam expansion of the novel AFFF agent. The nonionic hydrocarbon surfactants of component (D) in the novel AFFF agent have also a multiple function by acting as solubilizing agents for the $R_f$-surfactants of components (A) and (B) having poor solubility characteristics. They furthermore act as stabilizing agents, especially of AFFF agent sea water premixes and also influence the AFFF agent foam stability and foam drainage time as explained later. Furthermore they influence the viscosity of AFFF agents which is very critical especially in the case of 1% proportioning systems. Solvents of component (E) are used similarly as solubilizing agents for $R_f$-surfactants, but also act as foam stabilizers, to serve as refractive index modifiers for field calibration of proportioning, to reduce the viscosity of highly concentrated AFFF agents, and as anti-freezes. Whereas commercial 6% proportioning AFFF agents have high solvent contents of greater than 20%, this invention teaches the preparation of comparable formulations with excellent performance at solvent contents as low as 3%.

Some of the solvents present in the formulated AFFF agents are only present because they are carried into the product from the $R_f$-surfactant synthesis. Besides the contribution the ingredients so far listed may have on the performance of the novel AFFF agent, it must also be mentioned that these candidates were also selected because they have very low toxicity as shown in the experimental part of this application. As mentioned before other additives in the novel AFFF agent might be advantageous such as:

Corrosion inhibitors (for instance in the case where aqueous AFFF premixes are stored for several years in uncoated aluminum cans).

Chelating agents (if premixes of AFFF agents and very hard water are stored for longer periods of time).

Buffer Systems (if a certain pH level has to be maintained for a long period of time).

Anti-freeezes)if AFFF agents are to be stored and used at sub-freezing temperatures).

Polymeric thickening agents (if higher viscosities of AFFF agent -- water premixes are desired because of certain proportioning system requirements), and so on.

Today's commercial AFFF agents are only capable of use on 6 and 3% proportioning systems. The composition of the instant AFFF agents and the ranges of the amounts of the different active ingredients in these novel AFF agents will be expressed for 0.5 to 12% proportioning systems. If the concentration in a composition for 6% proportioning is doubled then such a concentrate can be used for a 3% proportioning system. Similarly if the concentration of such a 6% proportioning system is increased by a factor of 6 then it can be used as a 1% proportioning system. As comparative data in the experimental part will show it is possible to make such 1% proportioning systems primarily:

A. Because of the higher efficiency of the novel $R_f$-surfactants used and the smaller amounts therefore needed.

B. Because of the rather low amounts of solvents required in the new AFFF agents to achieve foam expansion ratios as specified by the military.

In the examples, references are made to specifications used by the industry and primarily the military and to proprietary tests to evaluate the efficiency of the claimed compositions. More specifically, the examples refer to the following specifications:

| | |
|---|---|
| Surface Tension and Interfacial Tension | ASTM D-1331-56 |
| Freezing Point | ASTM D-1177-65 |
| pH | ASTM D-1172 |

Sealability Test

Objective: To measure the ability of a fluorochemical AFFF formulation (at the end use concentration) to form a film across, and seal a cyclohexane surface.
Procedure: Ten mls of cyclohexane is pipetted into a 48 mm evaporating dish in the evaporometer cell. Helium flowing at 1000 cc per minute flushes the cyclohexane vapors from the cell through a 3 cm IR gas mounted on a PE 257 infrared spectrophotometer (a recording infrared spectrophotometer with time drive capability). The IR absorbence of the gas stream in the region of 2850 cm $^{-1}$ is continuously monitored as solutions of formulations are infused onto the surface. Formulations are infused onto the cyclohexane surface at a rate of 0.17 ml per minute using a syringe pump driven 1cc tuberculin syringe fitted with a 13 cm 22 gauge needle, whose needle is just touching the cyclohexane surface.

Once the absobence for "unsealed" cyclohexane is established, the syringe pump is started. Time zero is when the very first drop of formulation solution hits the surface. The time to 50% seal, percent seal at 30 seconds and 2minutes are recorded. Time to 50% seal relates well to film speed (see below) percent seal in 30 seconds and 2 minutes relate well to the efficiency and effectiveness of the film as a vapor barrier.

Film Speed Test

Objective: To determine the speed with which an AFFF film spreads across a cyclohexane surface.
Procedure: Fill a 6 cm aluminum dish one-half full with cyclohexane. Fill a 50 μl syringe with a 6% solution of the test solution. Inject 50 μl of the solution as rapidly and carefully as possible down the wall of the dish such that the solution flows gently onto the cyclohexane surface. Cover the dish with an inverted Petri dish. Start the timer at the end of the injection. Observe the film spreading across the surface and stop the timer the moment the film completely covers the surface and record the time.

Match Test

Objective: To roughly determine the sealing ability of an AFFF film.

Procedure:

Fill an aluminum weighing dish (58 x 15 mm) two-thirds with reagent cyclohexane. Carefully pour about 2 ml of test AFFF solution over the surface. Strike a wooden match, and after the initial flare-up of the match has subsided, immerse the flame quickly through the sealed surface and then retract it from the dish. The flame will be snuffed out. Repeat with additional matches until sustained ignition is achieved and note the number of matches used.

Fire Tests

The most critical test of the subject compositions is actual fire tests. The detailed procedures for such tests on 28, 50, and 1260 square foot fires are set forth in the U.S. Navy Specification MIL-F-24385 and its Amendments.

Procedure: Premixes of the compositions of this invention are prepared from 0.5 to 12% proportioning concentrates with tap or sea water, or the AFFF agent is proportioned by means of an in-line proportioning system. The test formulation in any event is applied at an appropriate use concentration.

The efficacy of the compositions of the present invention to extinguish hydrocarbon fires was proven repeatedly and reproducibly on 28-square foot (2.60 sq. m) gasoline fires are well as on 1260-square foot (117.05 sq. m) fires conducted on a 40 feet (12.19 m) in diameter circular pad. The tests were frequently conducted under severe environmental conditions with wind speeds up to 10 miles (16 km) per hour and under prevailing summer temperatures to 95° F (35° C). The fire performance tests and subsidiary tests -- foamability, film formation, sealability, film speed, viscosity, drainage time, spreading coefficient, and stability, all confirmed that the compositions of this invention performed better than prior art AFFF compositions.

The most important criteria in determing the effectiveness of a fire fighting composition are :

1. Control Time - The time to bring the fire under control or secure it after a fire fighting agent has been applied.
2. Extinguishing Time -The time from the initial application to the point when the fire is completely extinguished.
3. Burn-Back Time - The time from the point when the flame has been completely extinguished to the time when the hydrocarbon liquid reignites when the surface is subjected to an open flame.
4. Summation of % Fire Extinguished - When 50 or 1260 square foot (4.645 or 117.05 sq. m.) fires are extinguished the total of the "percent of fire extinguished" values are recorded at 10, 20, 30 and 40 second intervals. Present specifications for 50 square foot (4.645 sq. m.) require the "Summation" to fires be 225 or greater, for 1,260 square foot fires (117.05 sq. m.) 285 or greater.

28-Square Foot Fire Test

This test was conducted in a level circular pan 6 feet (1.83 m) in diameter (28 square feet -2.60 square meters), fabricated from $\frac{1}{4}$ inch (0.635 cm) thick steel and having sides 5 inches (12.70 cm) high, resulting in a freeboard of approximately 2-½ inches (6.35 cm) during tests. The pan was without leaks so as to contain gasoline on a substrate of water. The water depth was held to a minimum, and used only to ensure complete coverage of the pan with fule. The nozzle used for applying agent had a flow rate of 2.0 gallons per minute (g.p.m.) (7.57 1 per minute) at 100 pounds per square inch (p.s.i. (7.03 kg/sq. cm) pressure. The outlet was modified by a "wing tip" spreader having a ⅛-inch (3.175 mm) wide circular arc orifice 1-⅞inches (4.76 cm) long.

The premix solution in fresh water or sea water was at 70° ± 10° F (21° C ± 5.5° C). The extinguishing agent consistes of a 6-percent proportioning concentrate or its equivalent in fresh water or sea water and the fule charge was 10 gallons (37.85 l) of gasoline. The complete fuel charge was dumped into the diked area within a 60-second time period and the fuel was ignited within 60 seconds after completion of fueling and permitted to burn freely for 15 seconds before application of the extinguishing agent. The fire was extinguished as rapidly as possible by maintaining the nozzle 3-½ to 4 feet above the ground and angled upward at a distance that permitted the closest edge of the foam pattern to fall on the nearest edge of the fire. When the fire was extinguished, the time-for-extinguishment was recorded continuing distribution of the agent over the test area until exactly 3 gallons (11.36 l) of premix has been applied (90-second application time).

The burnback test was started whin 30 second after the 90-second solution application. A weighted 1-foot (30.48 cm) diameter pan having 2-inch (5.08 cm) side walls and charged with 1 quart (0.946 l) of gasoline was placed in the center of the area. The fuel in the pan was ignited just prior to placement. Burnback time commenced at the time of this placement and terminated when 25 percent of the fuel area (7 square feet -0.65 sq. meter), (36-inch diameter - 232.26 sq. cm), originally covered with foam was aflame. After the large test pan area sustained burning, the small pan was removed.

1260-Square-Foot Fire Test

This test was conducted in a level circular area 40 feet in diameter (1260-square-feet - 117.0 sq. m). The water depth was the minimum required to ensure complete coverage of the diked area with fuel. The nozzle used for applying the agent was designated to discharge 50 g.p.m. (189.27 l per minute) at 100 p.s.i. (7.07 kg/sq.cm).

The solution in fresh water or sea water was at 70° ± 10° F (21° C ± 5.50° C) and contained 6.0 ± 0.1% of the composition of this invention. Th fuel was 300 gallons (1135.6 l) of gasoline. No tests were conducted with wind speeds in excess of 10 miles (16 km) per hour. The complete fuel charge was dumped into the diked area as rapidly as possible. Before fueling for any test run, all extinguishing agent from the previous test run was removed from the diked area.

The fuel was ignited within 2 minutes after completion of fueling, and was permitted to burn freely fro 15 seconds before the application of the extinguishing agent.

The fire was extinguished as rapidly as possible by maintaining the nozzle 3-½ to 4 feet (1.07 to 1.22 m) above the ground and angled upward at a distance that permitted the closest edge of the foam pattern to fall on the nearest edge of the fire.

At least 85 percent of the fire was to be extinguished within 30 seconds, and the "percent of fire extinguished" values were recorded.

The examples presented below further demonstrate the instant invention but they are not intended to limit the invention in any way. The examples will also demonstrate:

1. the contribution of each component to the overall performance of the claimed AFFF concentrate, and
2. the superiority of the AFFF concentrate as compared to the prior art.

The pH of the compositions in the examples are generally in the range pH 7-8.5 unless otherwise mentioned.

EXPERIMENTAL PART

Tables 1 through 5 list amphoteric $R_f$-surfactants of Type A, anionic $R_f$-surfactants of Type B, ionic or amphoteric hydrocarbon surfactants of Type C, nonionic hydrocarbon surfactants of Type D and solvents of Type E which are used in the following examples:

Table 1

| Amphoteric* $R_f$-Surfactant | Name | Formula |
|---|---|---|
| | Amphoteric Fluorinated Surfactants used in Examples 1 to 77 | |
| A 1 | N-[3-(dimethylamino)propyl]-2 and 3-(1,1,2,2-tetrahydroperfluoroalkythio) succinamic acid | $R_fCH_2CH_2SCH(CO_2^-)CH_2CONH(CH_2)_3N^+H(CH_3)_2$ and $R_fCH_2CH_2SCH(CH_2CO_2^-)CONH(CH_2)_3N^+H(CH_3)_2$ |
| A 2 | N-methyl-N-(2'-N',N'-dimethylaminoethyl)-2 and 3-(1,1,2,2-tetrahydroperfluoroalkyl-thio) succinamic acid | $R_fCH_2CH_2SCH(CO_2^-)CH_2CON(CH_2)_2N^+H(CH_3)_2$ <br> $\qquad\qquad\qquad\qquad\qquad\qquad\ \ \ |$ <br> $\qquad\qquad\qquad\qquad\qquad\qquad\ \ CH_3$ |
| A 3 | N-ethyl-N-(2'-N',N'-dimethylaminoethyl)-2 and 3-(1,1,2,2-tetrahydroperfluoroalkyl-thio) succinamic acid | $R_fCH_2CH_2SCH(CO_2^-)CH_2CON(CH_2)_2N^+H(CH_3)_2$ <br> $\qquad\qquad\qquad\qquad\qquad\qquad\ \ \ |$ <br> $\qquad\qquad\qquad\qquad\qquad\qquad\ \ C_2H_5$ |
| A 4 | N-methyl-N-(2'-N',N'-dimethylaminopropyl)-2 and 3-(1,1,2,2-tetrahydroperfluoroalkyl-thio) succinamic acid | $R_fCH_2CH_2SCH(CO_2^-)CH_2CON(CH_2)_3N^+H(CH_3)_2$ <br> $\qquad\qquad\qquad\qquad\qquad\qquad\ \ \ |$ <br> $\qquad\qquad\qquad\qquad\qquad\qquad\ \ CH_3$ |
| A 5 | N-[2-(diethylamino)ethyl]-2(3)-(1,1,2,2-tetrahydroperfluorodecylthio) succinamic acid | $C_8F_{17}CH_2CH_2SCH(CO_2^-)CH_2CONH(CH_2)_2N^+H(C_2H_5)_2$ |
| A 6 | N-[3-(dimethylamino)propyl]-2(3)-(1,1,2,2-tetrahydroperfluorooctylthio) succinamic acid | $C_6F_{13}CH_2CH_2SCH(CO_2^-)CH_2CONH(CH_2)_3N^+H(CH_3)_2$ |
| A 7 | N-[3-(dimethylamino)propyl]-2(3)-(1,1,2,2-tetrahydroperfluorodecylthio) succinamic acid | $C_8F_{17}CH_2CH_2SCH(CO_2^-)CH_2CONH(CH_2)_3N^+H(CH_3)_2$ |
| A 8 | N-[3-(dimethylamino)propyl]-2(3)-(1,1,2,2-tetrahydroperfluorododecylthio) succinamic acid | $C_{10}F_{21}CH_2CH_2SCH(CO_2^-)CH_2CONH(CH_2)_3N^+H(CH_3)_2$ |

*As disclosed in Serial No. 538,432 (1/3/75), where $R_f$ is a mixture consisting principally of $C_6F_{13}$, $C_8F_{17}$, and $C_{10}F_{21}$ in the approximate ratio 1:2:1, and isomers as in Example No. A1. 30% solutions in actives for individual homologs.

Table 2

| Anionic $R_f$-Surfactant | Name | Formula - Actives ~100% or as Noted |
|---|---|---|
| | Anionic Fluorinated Surfactants* used in Examples 1 to 77 | |
| B1 | perfluoroalkanoic acid | $R_fCO_2H$ |
| B2 | potassium perfluoroalkanoate 25% | $R_fCO_2K$ - 25% in 10% hexylene glycol, ~15% t-butyl alcohol water |
| B3 | 1,1-dihydroperfluoroalkanoic acid | $R_fCH_2CO_2H$ |

Table 2-continued

Anionic Fluorinated Surfactants* used in Examples 1 to 77

| Anionic $R_f$-Surfactant | Name | Formula - Actives ~100% or as Noted |
|---|---|---|
| B4 | sodium 1,1,2,2-tetrahydroperfluoroalkylthio propanesulfonate | $R_fCH_2CH_2S(CH_2)_3SO_3Na$ |
| | $R_f =$ $C_6$ $C_8$ $C_{10}$ | |
| B5 | perfluoroheptanoic acid 75 25 0 | $C_6F_{13}CO_2H$ |
| B6 | perfluorononanoic acid 4 87 9 | $C_8F_{17}CO_2H$ |
| B7 | perfluoroundecanoic acid 0 11.5 88.5 | $C_{10}F_{21}CO_2H$ |
| B8 | potassium perfluoroheptanoate | $C_6F_{13}CO_2K$ - 25% as in B2 |

*where $R_f$ is typically a mixture of $C_6F_{13}$ (32%), $C_8F_{17}$ (62%) and $C_{10}F_{21}$ (6%), and traces of other homologs Table 3

Ionic (and Amphoteric) Surfactants used in Examples 1 to 77

| Ionic Surfactant | Type A-Anionic C-Cationic AM-Amphoteric | Name - % Actives as Noted or ~100% |
|---|---|---|
| C1 | AM | trimethylamine laurimide |
| C2 | AM | partial sodium salt of N-lauryl β-iminodipropionic acid (Deriphat 160C, General Mills 30%) |
| C3 | AM | N-lauryl, myristyl β-aminopropionic acid (Deriphat 170C, General Mills 50%) |
| C4 | C | cocoimidazolinium ethosulfate (Monaquate CIES Mona Industries) |
| C5 | AM | dimethyl(2-hydroxypropyl)amine laurimide |
| C6 | AM | dimethyl(2-hydroxypropyl)amine myristimide |
| C7 | AM | dimethyl(2-hydroxypropyl)amine palmitimide |
| C8 | AM | trimethylamine myristimide |
| C9 | AM | acylamidoammonium sulfonic acid betaine (Sulfobetaine CAW, Textilana 50%) |
| C10 | AM | dicarboxylic lauric derivative-imidazolimium amphoteric (Miranol H2M-SF, Miranol 38%) |
| C11 | A | sodium salt of ethoxylated lauryl alcohol sulfate (Sipon ES, Alcolac, 27%) |
| C12 | AM | disodium salt of N-lauryl β-iminodipropionic acid (Deriphat 160, General Mills) |

Table 4

Nonionic Surfactants used in Examples 1 to 77

| Nonionic Surfactant | Name % Actives as Noted or ~100% |
|---|---|
| D1 | octylphenoxypolyethoxyethanol (12) 99% Triton X-102, Rohm & Haas |
| D2 | polyoxyethylene (23) lauryl ether Brij 35, I.C.I. |
| D3 | octylphenoxypolyethoxyethanol (16) —70% Triton X-165, Rohm & Haas |
| D4 | octylphenoxypolyethoxyethanol (10) —99% Triton X-100, Rohm & Haas |
| D5 | octylphenoxypolyethoxyethanol (30) —70% Triton X-305, Rohm & Haas |
| D6 | nonylphenoxypolyethoxyethanol (20) Igepal CO-850, GAF |
| D7 | nonylphenoxypolyethoxyethanol (30) —70% Igepal CO-887, GAF |
| D8 | branched alcohol ethoxylate (15) Renex 31, Atlas Chemical Industries |

EXAMPLES 1 TO 4

AFFF agents having a composition as shown in Table 6 have identical compositions except that the $R_f$-group in the amphoteric $R_f$-surfactant varies from a pure perfluorohexyl to a pure perfluorooctyl to a pure perfluorodecyl group, and to a mixture of perfluorohexyl, perfluorooctyl and perfluorodecyl in a ratio of approximately 1:2:1.

As the surface tension data in Table 6 show, the lowest values are obtained with the pure $C_8$ isomer followed by the amphoteric $R_f$-surfactant with mixed $R_f$-groups. On the other hand, lowest interfacial tension values are obtained with the $C_6$ isomer and the $R_f$-isomer mixture. As a result the highest spreading coefficient of 6.5 dynes/cm is obtained with the $R_f$-mixture. $R_f$-mixture amphoteric fluorinated surfactants of Type A with mixed $R_f$-groups are, of course, from an economical standpoint, most desirable.

Table 5

Solvents used in Examples 1 to 77

| Solvent | Name |
|---|---|
| E1 | 1-butoxyethoxy-2-propanol |
| E2 | 1-butoxy-2-propanol/2-methyl-2,4-pentanediol ⅔ ratio |
| E3 | diethylene glycol monobutyl ether |
| E4 | 2-methyl-2,4-pentanediol |
| E5 | tetrahydrothiophene-1,1-dioxide |
| E6 | ethylene glycol |

Table 6

Effect of Amphoteric $R_f$-Surfactant (Component A) and its Homolog Content Example Nos. 1 to 4

| Amphoteric $R_f$-Surfactant solution | Various: (as stated) | | | |
|---|---|---|---|---|
| Anionic $R_f$-Surfactant | B1: 0.29 % | | | |
| Amphoteric Cosurfactant | C2: 8.33 % (30 % solids) | | | |
| Other Cosurfactant | C4: 0.83 % | | | |
| Nonionic Cosurfactant | D2: 2.08 % | | | |
| Solvent | E1: 5.00 % | | | |
| Water | Balance | | | |
| Example No. | 1 | 2 | 3 | 4 |
| $R_f$-surfactant A6, 30 % as is | 4.93 | | | |
| $R_f$-surfactant A7, 30 % as is | | 4.93 | | |
| $R_f$-surfactant A8, 100 % as is | | | 1.48 | |
| $R_f$-surfactant A1, 30 % as is | | | | 4.93 |
| Surface tension* dynes/cm | 17.7 | 16.9 | 18.0 | 17.2 |
| Interfacial tension* dynes/cm | 0.9 | 1.7 | 1.7 | 0.9 |
| Spreading coefficient* dynes/cm | 6.0 | 6.0 | 4.9 | 6.5 |

*3 percent dilution in distilled water; interfacial tension against cyclohexane

EXAMPLES 5 TO 10

AFFF agent compositions as listed in Table 7 have identical compositions with the exception of the anionic fluorinated surfactants of Type B, which vary from perfluorohexyl to a perfluorooctyl, to a perfluorodecyl group and mixtures of $R_f$-groups as defined in Table 2. Lowest surface tension data are obtained with perfluorooctyl and a mixed perfluoroalkyl group containing nonionic surfactants of Type B. Similarly, these preferred compositions show the fastest film speed.

Most important of the results shown in Table 7 is the fact that an AFFF agent not containing any of the anionic fluorinated surfactant of Type B has much higher surface tensions; therefore, a lower spreading coefficient, no film resealing properties and, in addition, a very slow film speed.

EXAMPLES 11 TO 17

Surface property measurements shown in Table 8 show that aqueous solutions of amphoteric $R_f$-surfactants of Type A, as disclosed in Ser. No. 538,432, have low surface tensions, but high interfacial tension (measured against hydrocarbons such as cyclohexane), and such aqueous solutions have, therefore, negative spreading coefficients. By the addition of amphoteric cosurfactants of Type C to aqueous solutions of amphoteric $R_f$-surfactants of Type A it is possible to lower the interfacial tension properties and achieve these very high spreading coefficients. Amphoteric cosurfactants of Type C are therefore referred to as interfacial tension depressants, even though they contribute to other properties of AFFF agents, such as foaming, stability, etc. Examples 11 to 16 show how the interfacial tension of a 0.1 percent aqueous solution of the amphoteric $R_f$-surfactant A5 is reduced by the addition of the preferred fatty aminimide surfactants of Type C, as listed in Table 3, from 7.1 dynes/cm to below 1.0 dynes/cm; the spreading coefficient is increased from -1.1 dynes/cm to up to 5.6 dynes/cm. A typical nonionic surfactant, D4, is much less effective.

Table 7

Effect of Anionic $R_f$-Surfactant and its Homolog Content
Example Nos. 5 to 10

| | | | | | |
|---|---|---|---|---|---|
| Amphoteric $R_f$-Surfactant Solution | A1: 4.93 % (30 % solids) | | | | |
| Anionic $R_f$-Surfactant | Various: 0.29 % | | | | |
| Amphoteric Cosurfactant | C2: 8.33 % (30 % solids) | | | | |
| Other Amphoteric Cosurfactant | C3: 1.66 % (70 % solids) | | | | |
| Nonionic Cosurfactant | D3: 2.97 % (70 % solids) | | | | |
| Solvent | E1: 5.00 % | | | | |
| Water | Balance | | | | |

| Example No. | | | | | |
|---|---|---|---|---|---|
| Anionic $R_f$-surfactant, as noted | none | B5 | B6 | B7 | B1 | B3 |
| $R_f$-homolog | | $C_6$ | $C_8$ | $C_{10}$ | mixture | mixture |
| Surface tension* dynes/cm | 19.5 | 18.1 | 17.5 | 17.7 | 17.7 | 17.5 |
| Interfacial tension* dynes/cm | 1.0 | 0.6 | 1.2 | 1.7 | 1.0 | 1.0 |
| Spreading coefficient* dynes/cm | 4.1 | 5.9 | 5.9 | 5.2 | 5.8 | 6.1 |
| Film speed, sec | very slow | 13 | 5 | 38 | 9 | 5 |
| Resealing property | none | good | good | poor | good | good |

*3 percent dilution in distilled water; interfacial tension against cyclohexane

Table 8

Surface Properties of Amphoteric $R_f$-Surfactant/
Amphoteric Cosurfactants Solutions

| | | |
|---|---|---|
| Amphoteric $R_f$-Surfactant Solution | A5: | 0.1 % |
| Cosurfactants - Variable | | 0.1 % |
| Water | | Balance |

| Example | Cosurfactant | Surface Tension dynes/cm | Interfacial Tension dynes/cm | Spreading Coefficient |
|---|---|---|---|---|
| 11 | none | 18.6 | 7.1 | −1.1 |
| 12 | C5 | 18.4 | 0.6 | 5.6 |
| 13 | C6 | 18.8 | 0.6 | 5.2 |
| 14 | C7 | 20.2 | 0.2 | 4.2 |
| 15 | C1 | 18.6 | 0.9 | 5.1 |
| 16 | C8 | 19.3 | 0.5 | 4.8 |
| 17 | D4 | 19.6 | 3.8 | 1.2 |

EXAMPLES 18 TO 23

The AFFF agents having a composition as listed in Table 9 are identical with the exception that the nonionic aliphatic cosurfactants of Type D vary. The comparison of the surface tension and interfacial tension data show that almost identical values within .5 of a dyne/cm are obtained and all samples show excellent compatibility with sea water while the only sample not containing nonionic hydrocarbon surfactant of Type D shows a heavy precipitate if diluted with sea water and aged at 150° F for 10 days.

Table 9

Composition and Evaluation of AFFF Agents
Example Nos. 18 to 23

| | | | | | | |
|---|---|---|---|---|---|---|
| Amphoteric $R_f$-Surfactant Solution | A1: 4.93 % (30 % solids) | | | | | |
| Anionic $R_f$-Surfactant | B1: 0.29 % | | | | | |
| Amphoteric Cosurfactant | C2: 8.33 % (30 % solids) | | | | | |
| Other Amphoteric Cosurfactant | C3: 1.66 % (50 % solids) | | | | | |
| Nonionic Cosurfactant | Various: 2.08 % (as 100 % solids) | | | | | |
| Solvent | E1: 5.00 % | | | | | |
| Water | Balance | | | | | |

| Example No. | 18 | 19 | 20 | 21 | 22 | 23 |
|---|---|---|---|---|---|---|
| Nonionic cosurfactant, as noted | none | D3 | D5 | D6 | D7 | D8 |
| Surface tension* dynes/cm | 18.0 | 17.3 | 17.4 | 17.0 | 16.9 | 17.5 |
| Interfacial tension* dynes/cm | 1.7 | 1.2 | 1.4 | 1.3 | 1.3 | 1.6 |
| Spreading coefficient* dynes/cm | 4.9 | 6.1 | 5.8 | 6.3 | 6.4 | 6.0 |
| Compatibility with sea water 6% dilution at 150° F for 10 days | heavy precipitate | clear | clear | clear | clear | clear |

*3 percent dilution in distilled water; interfacial tension against cyclohexane

EXAMPLES 24 TO 38

AFFF agents for 6 percent proportioning containing 2 percent by weight of variable solvents, but have otherwise identical compositions as shown in Table 10 were evaluated by using the Field Foam Test Method for determination of the foam expansion of a 6 percent dilution of the novel AFFF agents in synthetic sea water. As the data in Table 10 show, it is possible to obtain from expansion ratios ranging from 4.0 (high density foam) to 11.0 (lower density foam) by simply varying the type of solvent used in the AFFF agent. It is important from an ecological as well as economical standpoint that such a wide foam expansion range can be achieved with such a low (2 percent) solvent content.

half the amount of fluorine in the product, and about equal control time, extinguishing time and burnback time was achieved in comparison to FC-200 with the AFFF agent Example 42 containing just .8 percent fluorine vs. 2.1 percent fluorine in FC-200. The results indicate the higher efficiency of the novel AFFF agents, and that foam expansion is not as important a criterion to performance as are superior film properties.

Table 11

Comparative Fire Test Data* of AFFF Agents
Example Nos. 39 to 42

| | | |
|---|---|---|
| Amphoteric $R_f$-Surfactant Solution | A1: | Variable ( 30 % solids) |
| Nonionic Cosurfactant | D1: | Variable (100 % solids) |
| | A1:⎫⎬⎭ D1: | 1.4 (solids basis) |
| Anionic $R_f$-Surfactant | B1: | 0.35 % (100 % solids) |
| Amphoteric Cosurfactant | C1: | 2.25 % |
| Solvent | E2: | 6.25 % |
| Water | | Balance |

| Example No. | 39 | 40 | 41 | 42 | FC-200 |
|---|---|---|---|---|---|
| $R_f$-surfactant A1, % as is | 8.40 | 7.00 | 5.60 | 4.66 | |
| Nonionic surfactant D1, % as is | 1.80 | 1.50 | 1.20 | 1.00 | |
| % F in formula | 1.44 | 1.20 | 0.96 | 0.80 | 2.10 |
| Control time, sec | 28 | 30 | 34 | 34 | 33 |
| Extinguishing time, sec | 44 | 34 | 47 | 51 | 52 |
| Burnback time, min | 8:15 | 10:30 | 5:45 | 4:58 | 5:30 |
| Foam expansion | 5.5 | 5.6 | 5.4 | 4.7 | 7.0 |
| 25 % Drain time, min | 4:42 | 4:00 | 4:15 | 3:45 | 5:03 |

*6 % dilution in sea water, tested on 28 ft$^2$ fire

EXAMPLES 43 TO 45

AFFF agents having the composition as shown in Table 12 with variable anionic $R_f$-surfactants of Type B and variable solvents of Type E or containing no solvent at all were evaluated in 28 sq. ft. fire tests using a Table 10

Composition of AFFF Agents
Example Nos. 24 to 38

| | | |
|---|---|---|
| Amphoteric $R_f$-Surfactant Solution | A1: | 3.07 % |
| Anionic $R_f$-Surfactant | B1: | 0.19 % |
| Amphoteric Cosurfactant | C1: | 3.00 % |
| Nonionic Cosurfactant | D1: | 3.00 % |
| Solvent, Various | | 2.00 % |
| Water | | Balance |

| Example No. | Solvent | Foam Expansion | Example No. | Solvent | Foam Expansion |
|---|---|---|---|---|---|
| 24 | None | 4.2 | 32 | Butoxy-2-propanol | 11.0 |
| 25 | Diethylene glycol monobutyl ether | 7.9 | 33 | Dipropylene glycol monoethyl ether | 5.0 |
| 26 | Diethyl glycol diethyl ether | 4.2 | 34 | Propylene glycol monoethyl ether | 4.1 |
| 27 | N-Methyl-2-pyrrolidone | 4.1 | 35 | 2-Methyl-2,4-pentanediol | 6.2 |
| 28 | Tetrahydrothiophene-1,1-dioxide | 4.3 | 36 | Propoxy-2-propanol | 7.2 |
| 29 | t-Butanol | 6.3 | 37 | Dipropylene glycol | 4.0 |
| 30 | N,N-Dimethylformamide | 5.3 | 38 | 1-Butoxyethoxy-2-propanol | 11.0 |
| 31 | N,N-Dimethylacetamide | 4.5 | | | |

EXAMPLES 39 TO 42

AFFF agents having compositions as shown in Table 11 were evaluated and compared with a commercial AFFF agent, Light Water FC-200, in 28 sq. ft. fire tests. As the control time, extinguishing time, and burnback time data show, superior performance was achieved with the novel AFFF agents containing down to one- 2 gpm nozzle. As the test data in Table 12 show, high density foams with a foam expansion of less than 5 and as low as 3.7 are obtained with AFFF agents not containing any solvent while a solvent content of 35 percent increases foam expansion to as high as 8.5 with this AFFF agent composition. A comparison with the commercial FC-200 shows that slightly better extinguishing times are obtained in Example 43.

Table 12

Comparative Fire Test Data* of AFFF Agents
Example Nos. 43 to 45

| | | |
|---|---|---|
| Amphoteric $R_f$-Surfactant Solution | A1: | 7.1 (30 % solids) |
| Anionic $R_f$-Surfactant | | Variable (100 % solids) |
| Amphoteric Cosurfactant | C1: | 3.0 |
| Nonionic Cosurfactant | D1: | 3.0 |
| Solvent | | Variable |
| Water | | Balance |

| Example No. | 43 | 44 | 45 | FC-200 |
|---|---|---|---|---|

Table 12-continued

Comparative Fire Test Data* of AFFF Agents
Example Nos. 43 to 45

| | fresh | sea | fresh | sea | fresh | sea | fresh | sea |
|---|---|---|---|---|---|---|---|---|
| Anionic $R_f$-surfactant B1, % as is | .33 | | .33 | | | | | |
| Anionic $R_f$-surfactant B4, % as is | | | | | .50 | | | |
| Solvent E3 | 35 | | none | | none | | | |
| Extinguishing time, sec | 40 | 46 | 55 | 80 | 67 | 83 | 52 | 52 |
| Burnback time, min | 6:00 | 6:00 | 8:44 | 3:20 | 8:05 | 3:27 | 6:30 | 5:30 |
| Foam expansion | 8.5 | 7.7 | 3.8 | 3.8 | 4.8 | 3.7 | 7.0 | 7.0 |

*6 percent dilution in fresh or sea water, tested on 28 sq. ft. fire

EXAMPLES 46 TO 50

AFFF agents having a composition as shown in Table 13 were evaluated in 28 sq. ft. fire tests. The performance of these AFFF agents containing different cosurfactants of Type C show excellent control times (as low as 26 seconds), very short extinguishing times (as low as 37 seconds), and two of the compositions (Examples 48 and 50) did extinguish the fire by itself shortly after removal of the pan used in the 28 sq. ft. fire test, indicating the superior sealing capacity of the novel AFFF agents in comparison to the commercial products on the market.

Table 13
Comparative Fire Test Date* of AFFF Agents
Example Nos. 46 to 50

| Amphoteric $R_f$-Surfactant Solution | A1: | 5.9% (30% solids) | | | |
|---|---|---|---|---|---|
| Anionic $R_f$-Surfactant | B1: | 0.35% (100% solids) | | | |
| Ionic (and Amphoteric) Cosurfactants | | Variable | | | |
| Nonionic Cosurfactant | D1: | 1.2 | | | |
| Solvent | E : | 6.0 | | | |
| Water | | Balance | | | |
| Example No. | 46 | 47 | 48 | 49 | 50 |
| Cosurfactant - 1% solids | C3 | C4 | C1 | C1 | C1 |
| Cosurfactant - 2% solids | C2 | C2 | C9 | C10 | C2 |
| Control time, sec | 26 | 27 | 33 | 33 | 26 |
| Extinguishing time, sec | 39 | 37 | 48 | 45 | 38 |
| Burnback time, min | 7:31 | | 5:02 out+ | 7:56 | 4:35 out+ |
| Foam expansion | 5.9 | 6.2 | 6.7 | 5.9 | 6.6 |
| 25% Drain time, min | 5:19 | | 5:20 | 5:05 | 5:55 |

*Tested as a 6% dilution in sea water on 28 sq. ft. fires
+ Fire completely extinguished

EXAMPLE 51

An AFFF agent having the composition as shown in Table 14 was evaluated on a 1260 sq. ft. fire conducted on a level circular area 40 ft. in diameter fueled with 300 gallons of gasoline. A Rockwood FFF nozzle with double screen was used with a 50 gpm discharge. An excellent foam expansion of 9.0 was obtained and the fire was rapidly knocked down and almost completely extinguished within the diked area. Burnback was minimal and the "Summation of Percent Extinguishment" was 320 far exceeding Mil Specifications F-24385 (Navy).

Table 14
Fire Test of Preferred AFFF Agent on 1260 Ft. Fire Test
Example No. 51

| Amphoteric $R_f$-Surfactant Solution | A1: | 5.93% (30% solids) |
|---|---|---|
| Anionic $R_f$-Surfactant | B1: | 0.35% |
| Amphoteric Cosurfactant | C2: | 10.00% (30% solids) |
| Other Amphoteric Cosurfactant | C1: | 0.50% |
| Nonionic Cosurfactant | D1: | 1.20% |
| Solvent | E1: | 6.00% |
| Water | | Balance |
| Surface tension* dynes/cm | | 17.0 |
| Interfacial tension* dynes/cm | | 1.4 |
| Spreading coefficient* dynes/cm | | 6.2 |

Fire test performance as a 6 percent sea water dilution
Excellent knockdown and burnback
"Summation of Percent Extinguishment" - 320

| Foam expansion (50 gpm nozzle) | 9.0 |
|---|---|
| 25% Drainage | 4:00 |
| 50% Drainage | 8:41 |

*3% dilution in distilled water interfacial tension against cyclohexane

EXAMPLES 52 TO 56

AFFF agents having the compositions shown in Table 15 were tested as aerosol dispensed AFFF agents upon 2B fires (Underwriters Laboratory designation). The results show that the compositions were more effective in extinguishing the fires in a shorter time than either of the commerically available agents, Light Water FC-200 or FC-206. Example 54 shows that a composition protected against freezing is also effective as an extinguisher.

Table 15
Composition and Evaluation of Aerosol Dispensed AFFF Agents
Examples Nos. 52 to 55

| Example No. | 52 | | 53 | | 54 | | 55 | | 56 | | FC-200 | FC-206 |
|---|---|---|---|---|---|---|---|---|---|---|---|---|
| Amphoteric $R_f$-surfactant solution 4.9 % as is (30% solids) | A2 | | A2 | | A1 | | A1 | | A4 | | | |
| Anionic $R_f$-surfactant, % as is | B1, | 0.24 | B4, | 0.34 | B2, | 1.1 | B2, | 1.1 | B1, | 0.24 | | |
| Amphoteric cosurfactant, % as is | C1, | 3.0 | C1, | 3.0 | C2, | 5.0 | C2, | 5.0 | C2, | 2.0 | | |
| Other ionic surfactant, % as is | — | | — | | C4, | 0.5 | C4, | 0.5 | C4, | 0.5 | | |
| Nonionic cosurfactant, % as is | D1, | 1.0 | D1, | 1.0 | D1, | 1.75 | D1, | 1.75 | D1, | 1.0 | | |
| Solvent E4, 3% + % other as noted[1] | — | | — | | E5, | 20.0 | — | | — | | | |
| Buffer salts, 0.2%, type noted[1,3] | F1 | | F3 | | F1 | | F2 | | F4 | | | |
| Surface tension[4] dynes/cm | | 18.7 | | — | | 19.3 | | 18.1 | | 19.6 | 15.9 | 16.3 |
| Interfacial tension[4] dynes/cm | | 0.9 | | — | | .5 | | 1.9 | | 1.7 | 4.0 | 4.5 |
| Spreading coefficient[4] dynes/cm | | 5.0 | | — | | 3.7 | | 3.6 | | 3.3 | 4.7 | 3.8 |
| Fire Performance Characteristics[5] from Aerosol Can[2] on 2-B[6] Fires at a 6% Dilution | | | | | | | | | | | | |
| Discharge duration, sec | | 43 | | 32 | | 52 | | 64 | | 49 | 58 | 51 |
| Foam volume, liters | | 6.7 | | 6.5 | | 8.0 | | 7.0 | | 6.5 | 8 | 8 |
| Control time, sec | | 20 | | 24 | | 23 | | 26 | | 21 | 19 | 23 |

Table 15-continued
Composition and Evaluation of Aerosol Dispensed AFFF Agents
Examples Nos. 52 to 55

| Example No. | 52 | 53 | 54 | 55 | 56 | FC-200 | FC-206 |
|---|---|---|---|---|---|---|---|
| Extinguishing time, sec | 54 | 46 | 45 | 34 | 37 | 74 | 59 |

[1] The % solvent content and % buffer salts are noted for the actual aerosol charge after dilution of the concentrate to a 6% dilution; the remainder is water
[2] The aerosol container is a standard 20 oz. can containing a 430 gram charge of AFFF agent and a 48 gram charge of Propellant 12
[3] Buffer salts are
F1, Sorensen's phosphate at pH 7.5
F2, Sorensen's phosphate at pH 5.5
F3, McIlvaine's citrate/phosphate at pH 5.5
F4, Walpole's acetate at pH 5.5
[4] 6.0% dilution in distilled water; interfacial tension against cyclohexane
[5] discharge duration, sec - time to discharge aerosol completely at 70° F(21.1° C) foam volume, liters - total foam volume immediately after discharge control time, sec - time at which fire is secured, although still burning extinguishing time, sec - time for total extinguishment
[6] 2B fire - a 5 ft$^2$ (.465 sq. meters) area fire

EXAMPLES 57 AND 58

AFFF agents having the composition shown in Table 16 were compared to commercially available AFFF agents of both 6 percent and 3 percent proportioning types - 3M's Light Water FC-206 and FC-203 and National Foam's Aer-O-Water 6 and 3. The Examples 57 and 58 both demonstrate vastly superior film speeds (time to 50 percent seal), as well as more complete and highly persistent seals than available AFFF agents. These factors are of fundamental importance for an effective AFFF composition.

Table 16
Sealing Characteristics of AFFF Compositions
Example Nos. 57 and 58

| | | |
|---|---|---|
| Amphoteric R$_f$-Surfactant Solution | A1: | 5.0 % (30 % solids) |
| Anionic R$_f$-Surfactant | B1: | 0.3 % |
| Amphoteric Cosurfactant | C2: | 8.3 % (30 % solids) |
| Other Ionic Cosurfactants | | Variable |
| Nonionic Cosurfactant | | Variable |
| Solvent | E1: | 5.00 % |
| Water | | Balance |

| Example No. | 57 | 58 | Aer-O-Water 6 | Aer-O-Water 3 | FC 206 | FC 203 |
|---|---|---|---|---|---|---|
| Cosurfactant C1 | 0.4 | — | | | | |
| Cosurfactant C4 | — | 0.4 | | | | |
| Cosurfactant D3 | 3.0 | — | | | | |
| Cosurfactant D1 | — | 2.1 | | | | |
| Time to 50% seal | 5 | 8 | 18 | 18 | 25 | 12 |
| % seal in 30 sec | 98 | 97 | 45 | 30 | 85 | 72 |
| % seal in 120 sec | 98 | 98 | 87 | 91 | 96 | 87 |

| | |
|---|---|
| Surface area | - 20 cm$^2$ |
| Delivery rate | - 0.17 ml/min |
| Wave number | - 2930 cm$^{-1}$ |
| Cell path length | - 3 cm |
| Helium flow rate | - 1000 ml/min |

EXAMPLES 59 TO 63

AFFF agents having compositions as shown in Table 17 were submitted to fish toxicity studies using fathead minnows and bluegills. The evaluated AFFF agents have, as the results show, considerably lower toxicity than the control (Light Water FC-200) and, in addition, show a considerably lower chemical oxygen demand than the control primarily because of the lower solvent content in the novel AFFF agents.

Table 17
Composition and Evaluation of AFFF Agents
Example Nos. 59 to 63

| Example No. | 59 | 60 | 61 | 62 | 63 | FC-200 | |
|---|---|---|---|---|---|---|---|
| Amphoteric R$_f$-Surfactants | | | | | | | |
| Type + % as is | A1 5.60 | A2 5.60 | A3 5.60 | A1 4.93 | A4 4.93 | — | |
| Anionic R$_f$-Surfactants | | | | | | | |
| B1, % as is | 0.24 | 0.24 | 0.24 | 0.24 | 0.24 | — | |
| Cosurfactant C1, % as is | 3.00 | 3.00 | 3.00 | — | — | — | |
| Cosurfactant C2, % as is | — | — | — | 8.33 | 8.33 | — | |
| Cosurfactant C3, % as is | — | — | — | 1.66 | 1.66 | — | |
| Cosurfactant D1, % as is | 1.50 | 1.50 | 1.50 | 2.08 | 2.08 | — | |
| Solvents, Type + % | E2 6.0 | E2 6.0 | E2 6.0 | E1 5.0 | E1 5.0 | butyl carbitol 34.0 | |
| Type of Fish | BG | BG | BG | FM | FM | BG | FM |
| Fish toxicity ppm TL$_1$ | 484 | 700 | 859 | 611 | 483 | 49 | 312 |
| (FM = Fathead Minnows) TL$_{50}$ | 303 | 298 | 327 | 285 | 182 | 16 | 79 |
| (BG = Blue Gills) TL$_{99}$ | 190 | 129 | 124 | 133 | 69 | 5 | 20 |
| COD, g O$_2$/liter | 0.29 | 0.31 | 0.29 | 0.18 | | 0.70 | |

EXAMPLES 64 TO 68

AFFF agents for 6 percent proportioning containing different types of amphoteric cosurfactants of Type C and Type D but with otherwise identical compositions, were evaluated. The comparative evaluation data in Table 18 shown (a) that 3 percent solutions of the listed AFFF agents have spreading coefficients ranging from 4.5 to 5.8 dynes/cm, and (b) that the concentrates per se have a fish toxicity (fathead minnows) ranging from 114 to 524 ppm for a $TL_{50}$, indicating that the listed AFFF agents are considerably less toxic than Light Water FC-200, having a $TL_{50}$, of 79 ppm. Table 18 also shows that the listed AFFF agents have considerably lower chemical and biological oxygen demands (COD and $BOD_5$) than FC-200.

an ecology standpoint. Also listed in Table 19 are the chemical and biological oxygen demands (COD, $BOD_5$) of Examples 70 to 73. The very low COD values ranging from 0.19 to 0.22 g. of oxygen per liter are primarily due to the low solvent content in the novel AFFF agents.

Table 19

Composition and Evaluation of AFFF Agents
Example Nos. 69 to 73

| | | | | | | |
|---|---|---|---|---|---|---|
| Amphoteric $R_f$-Surfactant Solution | | A1: | 4.93 % ( 30 % Solids) | | | |
| Anionic $R_f$-Surfactant | | B1: | 0.29 % (100 % Solids) | | | |
| Amphoteric Cosurfactant and Nonionic Cosurfactants | | : | Variable | | | |
| Solvent | | E1: | 5.00 % | | | |
| Water | | | Balance | | | |

| Example No. | 69 | 70 | 71 | 72 | 73 | FC-200 |
|---|---|---|---|---|---|---|
| Cosurfactant C2, % as is | 8.33 | 8.33 | 8.33 | 5.66 | 5.66 | — |
| Cosurfactant C3, % as is | 1.66 | 1.66 | 1.66 | — | — | — |
| Cosurfactant D1, % as is | 2.08 | — | — | 0.75 | — | — |
| Cosurfactant D2, % as is | — | — | 2.08 | — | 0.75 | — |
| Cosurfactant D3, % as is | — | 2.97 | — | — | — | — |
| Surface Tension,* dynes/cm | 18.1 | 18.0 | 18.2 | 18.1 | 18.2 | 15.9 |
| Interfacial Tension,* dynes/cm | 1.3 | 1.5 | 1.5 | 2.5 | 2.8 | 4.0 |
| Spreading Coefficient, dynes/cm | 5.2 | 5.1 | 4.9 | 4.0 | 3.6 | 4.7 |
| Fish Toxicity, ppm, $TL_1$ | 611 | 434 | 480 | >1000 | >1000 | 312 |
| (Fathead Minnows) $TL_{50}$ | 285 | 294 | 318 | >1000 | >1000 | 79 |
| $TL_{99}$ | 133 | 198 | 211 | >1000 | >1000 | 20 |
| COD, g O/g | — | 0.19 | 0.22 | 0.20 | 0.19 | 0.70 |
| BOD, mg O/liter | — | 875 | 906 | 5600 | 6830 | 15600 |

*3 % dilution in distilled water; interfacial tension against cyclohexane

Table 18

Composition of AFFF Agents
Example Nos. 64 to 68

| | | | |
|---|---|---|---|
| Amphoteric $R_f$-Surfactant Solution | A1: | 4.93 % ( 30 % Solids) | |
| Anionic $R_f$-Surfactant | B1: | 0.29 % (100 % Solids) | |
| Amphoteric Cosurfactant | C2: | 8.33 % ( 30 % Solids) | |
| Other Cosurfactants | | Variable | |
| Solvent | E1: | 5.00 % | |
| Water | | Balance | |

| Example No. | 64 | 65 | 66 | 67 | 68 | FC-200 |
|---|---|---|---|---|---|---|
| Cosurfactant C1, % as is | — | 0.42 | — | — | — | — |
| Cosurfactant C3, % as is | 1.66 | — | 0.84 | — | — | — |
| Cosurfactant C4, % as is | — | — | — | 0.42 | 0.84 | — |
| Cosurfactant D1, % as is | — | — | 2.08 | 2.08 | 2.08 | — |
| Cosurfactant D3, % as is | 2.97 | 2.97 | — | — | — | — |
| Surface Tension,* dynes/cm | 18.0 | 7.2 | 18.2 | 18.4 | 18.4 | 15.9 |
| Interfacial Tension,* dynes/cm | 1.5 | 1.6 | 1.9 | 1.4 | 1.3 | 4.0 |
| Spreading Coefficient, dynes/cm | 5.1 | 5.8 | 4.5 | 5.2 | 4.9 | 4.7 |
| Fish Toxicity, ppm, $TL_1$ | 434 | 880 | 480 | 447 | 160 | 312 |
| (Fathead Minnows) $TL_{50}$ | 294 | 524 | 318 | 228 | 114 | 79 |
| $TL_{99}$ | 198 | 313 | 211 | 116 | 82 | 20 |
| COD, g $O_2$/g | 0.19 | 0.20 | 0.28 | 0.26 | 0.25 | 0.70 |
| BOD, mg $O_2$/liter | 876 | 1023 | 12300 | 10000 | 5830 | 15600 |

*3 % dilution in distilled water; interfacial tension against cyclohexane

Further optimized AFFF agents for 6 percent proportioning containing different types and amounts of amphoteric and nonionic cosurfactants of Types C and D, but identical amphoteric and anionic Rf-surfactants of Types A and B, were evaluated. The comparative evaluation data in Table 19 show that spreading coefficients ranging from 3.6 to 5.1 dynes/cm are obtained, while fish toxicity data of the AFFF agent concentrates range from 294 to larger than 1000 ppm for a $TL_{50}$ for fathead minnows. A $TL_{50}$ of larger than 1000 ppm is considered non-toxic and products like AFFF agents Examples 72 and 73 are therefore most desirable from

EXAMPLE 74

An AFFF agent having a composition as shown for Example 72 and solutions thereof in synthetic sea water were selected to show the low or non corrosive character of the novel AFFF agents. Corrosion tests carried out in accordance with U.S. military requirement MIL-F-24385 Amendment 8, June 20, 1974 show, as presented in Table 20, that corrosion observed with different metals and alloys is 10 to 100 times smaller than the maximum tolerance levels specified in MIL-F-24385, Amendment 8.

Table 20

| | | AFFF Agent Example No. 72 | | MIL-F-24385 Requirement Amendment 8 |
|---|---|---|---|---|
| | Property | Average* | Maximum | (June 20, 1974) |
| A. | Corrosion (milligrams/dm day) Partial submersion of metal coupon in liquid for 38 days at 98° F (38° C) | | | |
| | Dilution            Alloy | | | |
| | Concentrate     Cold rolled steel SAE 1010 | 0.16 | 0.24 | 25 maximum |
| | Concentrate     Corrosion-resistant steel (CRES 304) | 0.2 | 0.2 | 25 maximum |

Table 20-continued

|   | Property |   | AFFF Agent Example No. 72 Average* | Maximum | MIL-F-24385 Requirement Amendment 8 (June 20, 1974) |
|---|---|---|---|---|---|
|   | 6% Sea Water | Cupro-nickel (90% Cu 10% Ni) | 0.42 | 0.59 | 10 maximum |
|   | Concentrate | Aluminum 6061T6 | 0 | 0 | Not specified |
| B. | Total immersion of metal coupons in liquid at ambient temperature for 60 days (milliinches/year) | | | | |
|   | Dilution | Alloy | | | |
|   | 90% Sea Water | Cold rolled steel SAE 1010 | 0.39 | 0.78 | Not specified |
|   | 90% Sea Water | Cupro nickel (90% Cu 10% Ni) | 0.33 | 0.73 | Not specified |
|   | 90% Sea Water | Monel 400 | 0 | 0.05 | Not specified |
|   | 90% Sea Water | Bronze 905 (milligrams) | 7 | 8 | Not specified |
| C. | Localized Corrosion - 60 days Sumbersion of rubber girded metal coupon in liquid at ambient temperature for 60 days | | | | |
|   | Dilution | Alloy | | | |
|   | None | CRES 304 | No pits at 10 X | No pits at 10 X | No visible pitting at 10 X magnification |

*Average of 4 tests

EXAMPLES 75 TO 77

AFFF agents were formulated containing identical ingredients but at progressively higher concentrations. The data show that concentrates can be prepared for 3 percent, and even 1 percent proportioning, which are stable and perform well. Six percent proportioning concentrates such as National Foam, Aer-O-Water 6 and Light Water FC-200 containing 18 percent and 34 percent, respectively, of solvents, contain so much solvent that they could not be formulated as 1 percent proportioning concentrates.

Table 21
Formulation of Highly Concentrated AFFF Agents
Example Nos. 75 to 77

| Example No. Proportioning Type | 75 6% | | 76 3% | | 77 1% | |
|---|---|---|---|---|---|---|
|   | % as is | % solids | % as is | % solids | % as is | % solids |
| Amphoteric $R_f$-surfactant A1 | 3.33 | 1.00 | 6.66 | 2.00 | 20.0 | 6.0 |
| Anionic $R_f$-surfactant B2 | 0.80 | 0.20 | 1.60 | 0.40 | 4.80 | 1.20 |
| Amphoteric cosurfactant C12 | 1.70 | 1.70 | 3.40 | 3.40 | 10.20 | 10.20 |
| Nonionic cosurfactant D1 | 0.50 | 0.50 | 1.00 | 1.00 | 3.00 | 3.00 |
| Solvent | 6.00 | — | 12.00 | — | 36.00 | — |
| Water | 87.67 | — | 75.34 | — | 26.00 | — |
| Total | 100.00 | 3.40 | 100.00 | 6.80 | 100.00 | 20.40 |
| Freezing point ° F (° C) | 26 (−3) | | 20 (−7) | | 11 (−12) | |
| pH | 7.5 | | 7.5 | | 7.5 | |
| Chloride content (ppm) | <50 | | <50 | | <50 | |

What is claimed is:

1. An aqueous film forming concentrate composition for extinguishing or preventing fires by suppressing the vaporization of flammable liquids, said composition consisting essentially of
A. 0.5 to 25% by weight of an amphoteric fluorinated surfactant represented by the formulae

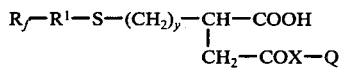   I

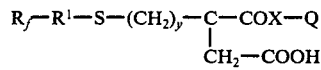   II and its isomer

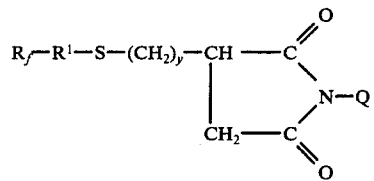   III wherein
$R_f$ is straight or branched chain perfluoroalkyl of 1 to 18 carbon atoms or said perfluoroalkyl substituted by perfluoroalkoxy of 2 to 6 carbon atoms,
$R^1$ is branched or straight chain alkylene of 1 to 12 carbon atoms, alkylenethioalkylene of 2 to 12 carbon atoms, alkyleneoxyalkylene of 2 to 12 carbon atoms or alkyleneiminoalkylene of 2 to 12 carbon atoms wherein the nitrogen atom contains as a third substituent, hydrogen or alkyl of 1 to 6 carbon atoms,
$y$ is 1 zero,
X is oxygen or −NR, wherein R is hydrogen, lower alkyl of 1 to 6 carbon atoms, hydroxy-alkyl of 1 to 6 carbon atoms, or R together with Q forms a piperazine ring, and
Q is a nitrogen containing group selected from
1. an aliphatic amino group selected from $$-(R^2)_k-N\begin{matrix}R^3\\ \\R^4\end{matrix} \quad (1a)$$

$$-(R^2)_k-\overset{+}{N}\begin{matrix}R^3\\ \diagup\\ \diagdown R^5 \quad A^-\\R^4\end{matrix} \quad \text{and} \quad (1b)$$

$$-(R^2)_k-\overset{+}{N}\begin{matrix}R^3\\ \diagup\\ \diagdown G^-\\R^4\end{matrix} \quad (1c)$$

wherein
R² is a linear or branched alkylene of 2 to 12 carbon atoms, oxygen or sulfur interrupted linear or branched alkylene of up to 60 carbon atoms, or hydroxyl substituted alkylene. Preferably R² is a straight chain or branched alkylene of 2 to 5 carbon atoms;

k is 1 or zero, with the provision that if X is oxygen, k is 1;

R³ and R⁴ are independently of each other hydrogen, alkyl group, substituted alkyl group of 1 to 20 carbon atoms; phenyl group, alkyl or halogen substituted phenyl group of 6 to 20 carbon atoms, polyethoxy or polypropoxy group of 2 to 20 alkoxy units with the proviso that if X is oxygen, R³ and R⁴ are not hydrogen. The alkyl substituents can be alkyl of 1 to 5 carbon atoms, dienyl, hydroxyl, carboxyl, halogen, alkylene dialkylphosphonate such as methylene-diethylphosphonate or a group

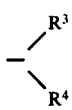

Phenyl substituents can be methyl, halogen or hydroxyl. Preferably R³ and R⁴ are alkyl groups of 1 to 4 carbons.

A⁻ is any anion which forms an ammonium salt of the formula NH₄⁺A⁻ having a solubility in water of at least about 1%.

Anion A⁻ is derived from alkyl halides, benzene or chlorobenzene sulfonate esters of alkyl alcohols and methyl and ethyl sulfates. A⁻ is preferably Cl⁻ or CH₃CH₂OSO₃⁻.

R⁵ is hydrogen, an alkyl group or hydroxyalkyl group, aralkyl or groups of the formula —(CH₂)$_n$—COO—alkyl, said alkyl group having 1 to 18 carbons. Preferably, R⁵ is methyl, ethyl, propyl, butyl or benzyl.

G⁻ is selected from the groups

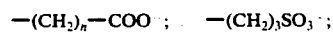

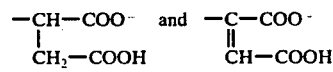

where n is 1 to 5;

2. cyclic amino groups selected from

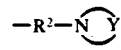 (2a)

 (2b)

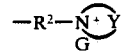 (2c)

wherein Y is a diradical group of the formulae:
—(CH₂)₄—
—(CH₂)₅—
—(CH₂)₂—O—(CH₂)₂—

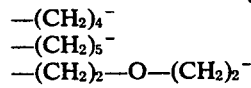, wherein R², R⁵, A⁻ and G⁻ are as defined above,
R⁷ and R⁸ are independent hydrogen, a lower alkyl or hydroxy-lower alkyl group of 1 to 6 carbon atoms, with the provision, that if X is oxygen, R⁸ cannot be hydrogen.

3. aromatic amino groups selected from

 (3a)

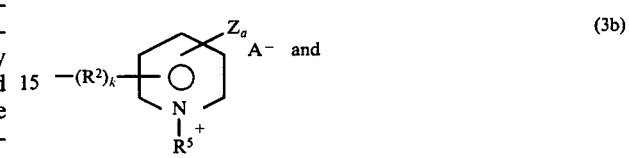 (3b)

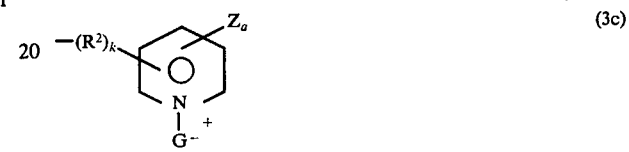 (3c)

4. fused-ring aromatic amino group selected from

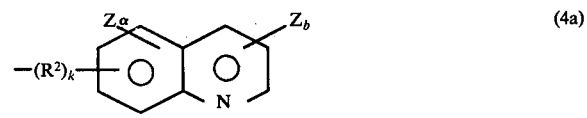 (4a)

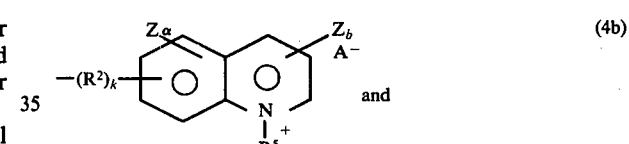 (4b)

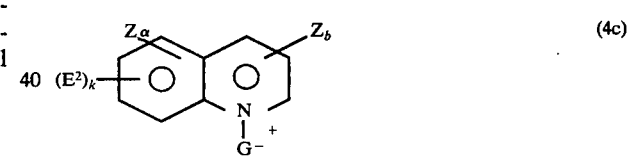 (4c)

wherein
Z is halogen or methyl,
a + b is an integer from 0–3; and 5. a heterocyclic amino group of the formula
5a. —(R²)$_k$—E
5b. —(R²)$_k$—E⁺—R⁵ A⁻
5c. —(R²)$_k$—E⁺—G⁻
where k is one or zero and
E is selected from N-hydroxyalkyl or N-amino-alkyl, substituted pyrrole, pyrazole, imidazole, triazole, indole or indazole, hydroxyalkyl and aminoalkyl ring-substituted pyridazine, pyrimidino, pyrazino or quinoxalino; B. 0.1 to 5% by weight of an anionic fluorinated surfactant represented by the formula R$_f$Q$_m$Z
wherein
R$_f$ is a fluorinated saturated monovalent non-aromatic radical containing from 3 to 20 carbon atoms in which the carbon atoms of the chain are substituted only by fluorine, chlorine or hydrogen atoms with no more than one hydrogen or chlorine atom for every two carbon atoms, and in which a divalent oxygen or trivalent nitrogen atom, bonded only to carbon atoms, can be present in the skeletal chain;

$Q_m$, where $m$ is an integer of 0 to 1, is a multivalent linking group comprising alkylene, sulfonamido alkylene and carbonamido alkylene radicals; and Z is a water solubilizing polar group comprising anionic radicals;

C. 0.1 to 25% by weight of an ionic non-fluorochemical water soluble surfactant selected from anionic, cationic and amphoteric surfactants wherein
  1. anionic surfactants are selected from carboxylic acids, sulfuric esters, alkane sulfonic acids and alkylaromatic sulfonic acids,
  2. cationic surfactants are selected from amine salts and quaternary ammonium compounds, and
  3. amphoteric surfactants which contain in the same molecule an amino group and a group selected from carboxy, sulfuric ester, alkane sulfonic acid and aromatic sulfonic acid group or aminimides;

D. 0.1 to 40% by weight of a nonionic nonfluorochemical surfactant selected from polyoxyethlylene derivatives of alkylphenols, linear or branched alcohols, glucosides and block polymers of polyoxytheylene and polyoxypropylene;

E. 0 to 70% by weight of a solvent selected from ether alcohols or alcohols, and F. water in the amount to make up the balance of 100%, said concentrate, upon dilution with water, being capable of forming a foam which drains to form a tough, durable, film on the surface of a flammable liquid thereby inhibiting the release of vapors therefrom.

2. A composition of claim 1 wherein component (C) the ionic non-fluorochemical surfactant is
  1. anionic surfactant which is selected from carboxylic or sulfonic acids or sulfuric acid esters, or
  2. cationic surfactant which is selected from amine salts and quaternary ammonium compounds, or
  3. amphoteric non-fluorocchemical surfactant which contain in the same molecule amino and carboxy or sulfo groups or is an aminimide; and
  component E, the solvent is selected from 1-butoxyethoxy-2-propanol, hexylene glycol and diethylene glycol monobutyl ether.

3. A composition of claim 1 consisting essentially of
A. 1.0 to 3.5% by weight of amphoteric fluorinat ed surfactant,
B. 0.1 to 2.5% by weight of anionic fluorinated surfactant,
C. 0.1 to 4.0% by weight of ionic non-fluorochemical surfactant,
D. 0.1 to 8.0% by weight of nonionic non-fluorochemical surfactant,
E. 0 to 20% by weight of solvent and water in the amount to make up the balance of 100%

4. A composition of claim 3 consisting essentially of
A. N--2 and 3-(1,1,2,2-tetrahydroperfluoroalkythio) succinamic acid
B. perfluoroalkanoic acid or potassium salt thereof
C. partial sodium salt of N-lauryl $\beta$-iminodipropionic acid
D. octylphenoxypolyethoxyethanol
E. 1-butoxyethoxy-2-propanol 5. A composition of claim 3 consisting essentially of
A. N--2 and 3-(1,1,2,2,-tetrahydroperfluoroalkythio) succinamic acid
B. perfluoroalkanoic acid or potassium salt thereof
C. partial sodium salt of N-lauryl $\beta$-iminodipropionic acid and cocoimidazolinium ethosulfate
D. octylphenoxypolyethoxyethanol
E. 1-butoxyethoxy-2-propanol.

6. An aqueous film-forming composition for extinguishing or preventing fires in an aerosol form, said composition of claim 1 in diluted form and an inert propellant.

* * * * *